US010768797B2

(12) United States Patent
Song et al.

(10) Patent No.: US 10,768,797 B2
(45) Date of Patent: Sep. 8, 2020

(54) METHOD, APPARATUS, AND SYSTEM FOR GENERATING BODY MARKER INDICATING OBJECT

(71) Applicant: SAMSUNG MEDISON CO., LTD., Hongcheon-gun (KR)

(72) Inventors: Min-Jung Song, Hongcheon-gun (KR); Min-ju Lee, Hongcheon-gun (KR); Seung-ju Lee, Hongcheon-gun (KR); Jin-gyu Seo, Namyangju-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 301 days.

(21) Appl. No.: 14/714,735

(22) Filed: May 18, 2015

(65) Prior Publication Data

US 2016/0170618 A1   Jun. 16, 2016

(30) Foreign Application Priority Data

Dec. 15, 2014   (KR) .......................... 10-2014-0180499

(51) Int. Cl.
*G06F 3/0482*   (2013.01)
*G06F 3/0484*   (2013.01)
(Continued)

(52) U.S. Cl.
CPC ............ *G06F 3/04845* (2013.01); *A61B 8/14* (2013.01); *A61B 8/461* (2013.01); *A61B 8/463* (2013.01); *A61B 8/465* (2013.01); *A61B 8/467* (2013.01); *A61B 8/468* (2013.01); *G06F 3/0482* (2013.01); *G06F 3/04842* (2013.01); *G06F 3/04883* (2013.01); *G06T 11/60* (2013.01);
(Continued)

(58) Field of Classification Search
CPC ............ G06F 3/04845; G06F 3/04842; G06F 3/0482; G06F 3/04883; A61B 8/14; A61B 8/461; A61B 8/463; A61B 8/465; A61B 8/468; G16H 40/63; G06T 11/60
See application file for complete search history.

(56) References Cited

U.S. PATENT DOCUMENTS 4,416,286 A * 11/1983 Iinuma .................... A61B 8/06
                                                            600/441
5,367,498 A * 11/1994 Takashi ................ G01S 7/6227
                                                            367/107
(Continued)

FOREIGN PATENT DOCUMENTS

CN           102203714 A      9/2011
EP             2783635 A1    10/2014
(Continued)

OTHER PUBLICATIONS

Communication dated May 6, 2016, issued by the European Patent Office in counterpart European Application No. 15163220.5.
(Continued)

*Primary Examiner* — Joanne M Hoffman
(74) *Attorney, Agent, or Firm* — Sughrue Mion, PLLC

(57) ABSTRACT

A method of generating a body marker includes selecting a first body marker from among a plurality of prestored body markers based on an object shown in a medical image; generating a second body marker by modifying a shape of the first body marker according to a user input; and displaying the second body marker.

30 Claims, 21 Drawing Sheets

(51) Int. Cl.
  *G06F 3/0488* (2013.01)
  *G06T 11/60* (2006.01)
  *A61B 8/14* (2006.01)
  *A61B 8/00* (2006.01)
  *G16H 40/63* (2018.01)
  *A61B 8/08* (2006.01)
  *G06F 19/00* (2018.01)

(52) U.S. Cl.
  CPC ............ *G16H 40/63* (2018.01); *A61B 8/0866* (2013.01); *A61B 8/0891* (2013.01); *A61B 8/4405* (2013.01); *A61B 8/4427* (2013.01); *A61B 8/4472* (2013.01); *A61B 8/565* (2013.01); *G06F 19/321* (2013.01); *G06T 2200/24* (2013.01); *G06T 2210/41* (2013.01)

(56) References Cited

U.S. PATENT DOCUMENTS

| | | | | |
|---|---|---|---|---|
| 9,005,128 B2 * | 4/2015 | Imamura | ........... | A61B 8/14 382/128 |
| 9,146,674 B2 * | 9/2015 | Karlsson | ........... | G06F 3/04883 |
| 9,211,105 B2 * | 12/2015 | Hyun | ........... | A61B 8/00 |
| 2002/0167549 A1 * | 11/2002 | Cupples | ........... | A61B 8/0825 715/835 |
| 2002/0173721 A1 * | 11/2002 | Grunwald | ........... | A61B 8/00 600/437 |
| 2004/0122310 A1 * | 6/2004 | Lim | ........... | A61B 8/00 600/426 |
| 2005/0027193 A1 * | 2/2005 | Mitschke | ........... | A61B 6/12 600/427 |
| 2005/0122343 A1 * | 6/2005 | Bailey | ........... | G06T 3/0037 345/619 |
| 2005/0171430 A1 * | 8/2005 | Zhang | ........... | A61B 8/0825 600/437 |
| 2005/0245825 A1 * | 11/2005 | Krantz | ........... | G06T 7/0012 600/443 |
| 2008/0177182 A1 * | 7/2008 | Takimoto | ........... | A61B 8/06 600/441 |
| 2009/0076385 A1 * | 3/2009 | Jackson | ........... | A61B 8/0825 600/437 |
| 2010/0030079 A1 * | 2/2010 | Hamada | ........... | A61B 8/14 600/443 |
| 2010/0191114 A1 * | 7/2010 | Hyun | ........... | A61B 8/00 600/443 |
| 2010/0321324 A1 | 12/2010 | Fukai et al. | | |
| 2011/0208052 A1 | 8/2011 | Entrekin | | |
| 2011/0282199 A1 * | 11/2011 | Lee | ........... | A61B 5/1075 600/437 |
| 2012/0131488 A1 * | 5/2012 | Karlsson | ........... | G06F 3/04883 715/771 |
| 2013/0137988 A1 * | 5/2013 | Bregman-Amitai | ........... | A61B 8/4254 600/459 |
| 2013/0253316 A1 | 9/2013 | Choi | | |
| 2013/0324849 A1 * | 12/2013 | Park | ........... | A61B 8/463 600/440 |
| 2014/0088427 A1 * | 3/2014 | Tashiro | ........... | A61B 8/08 600/443 |
| 2014/0104311 A1 | 4/2014 | Park et al. | | |
| 2014/0107484 A1 * | 4/2014 | Hyun | ........... | G06T 11/206 600/441 |
| 2014/0129990 A1 * | 5/2014 | Xin | ........... | G06F 3/017 715/849 |
| 2014/0221836 A1 | 8/2014 | Takeda et al. | | |
| 2014/0296711 A1 | 10/2014 | Lee | | |
| 2014/0324475 A1 | 10/2014 | Ochi et al. | | |
| 2016/0066887 A1 * | 3/2016 | Hyun | ........... | A61B 8/463 600/440 |

FOREIGN PATENT DOCUMENTS

| | | |
|---|---|---|
| JP | 2000175910 A | 6/2000 |
| JP | 2014-124269 A | 7/2014 |
| JP | 2014-150804 A | 8/2014 |
| KR | 10-2013-0107882 A | 10/2013 |

OTHER PUBLICATIONS

Communication dated Aug. 16, 2019, issued by the State Intellectual Property Office of P.R. China in counterpart Chinese Application No. 201510455280.X.

Communication dated Nov. 29, 2019, from the European Patent Office in counterpart European Application No. 15163220.5.

* cited by examiner

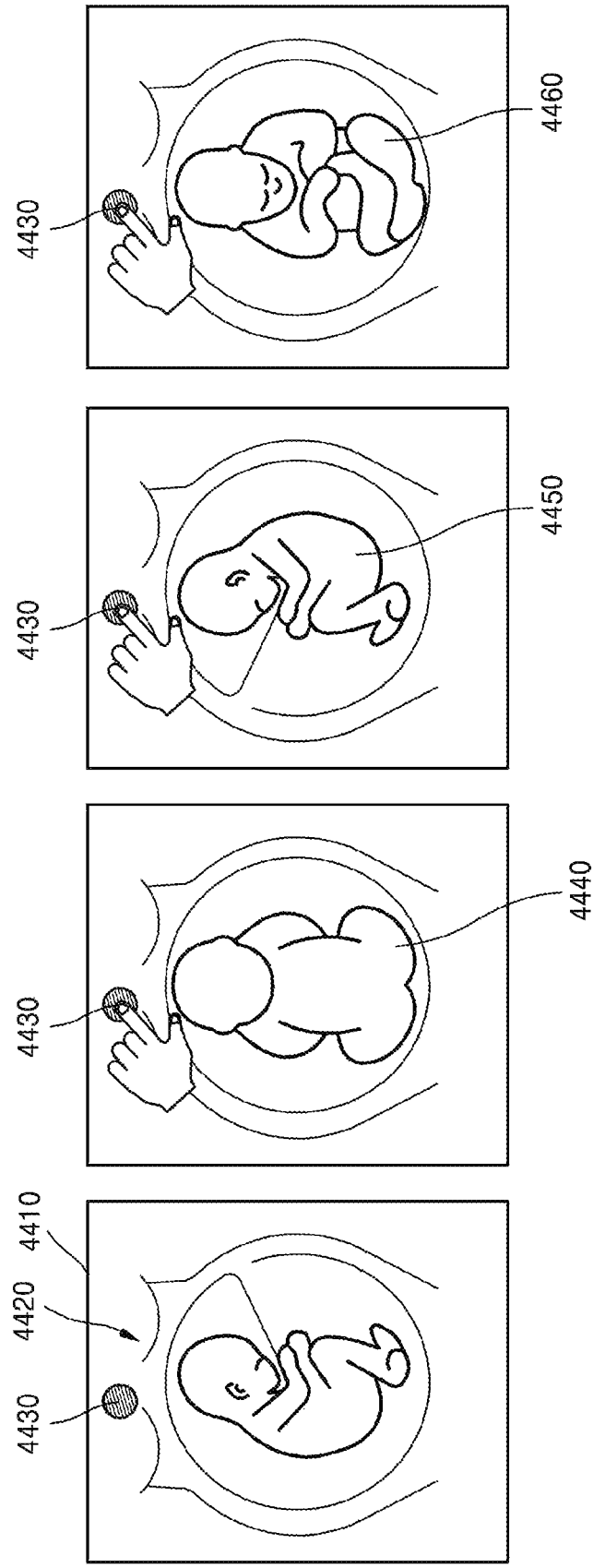

FIG. 12A
FIG. 12B
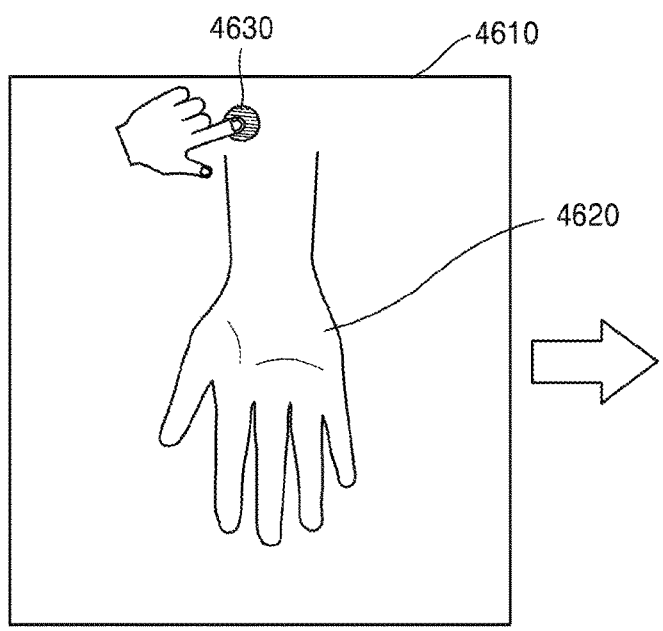
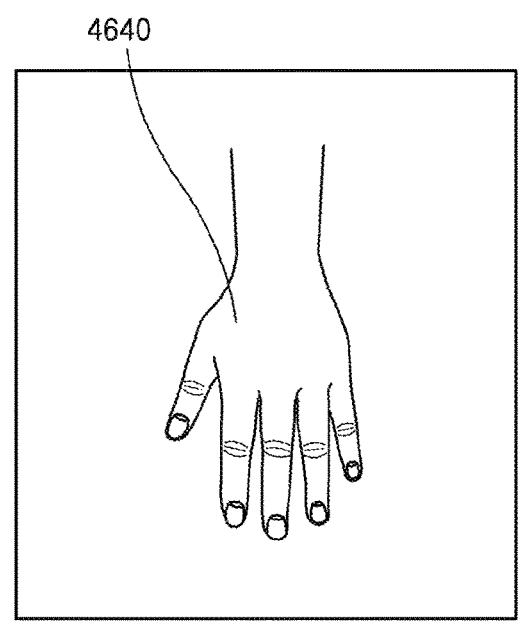

METHOD, APPARATUS, AND SYSTEM FOR GENERATING BODY MARKER INDICATING OBJECT

RELATED APPLICATION

This application claims the benefit of Korean Patent Application No. 10-2014-0180499, filed on Dec. 15, 2014, in the Korean Intellectual Property Office, the disclosure of which is incorporated herein in its entirety by reference.

BACKGROUND

1. Field

One or more exemplary embodiments relate to a method, an apparatus, and a system for generating a body marker indicating an object.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

In general, a body marker is added to an ultrasound image when a user selects one of pre-generated body markers. However, it may be difficult to accurately determine a shape or an orientation of an object shown in the ultrasound image based on the body marker shown in the ultrasound image. Also, it may require a large amount of time for the user to select one of the pre-generated body markers.

SUMMARY

One or more exemplary embodiments include a method, an apparatus, and a system for generating a body marker indicating an object. Also, a non-transitory computer-readable recording medium having recorded thereon a program, which, when executed by a computer, performs the method.

Additional aspects will be set forth in part in the description which follows and, in part, will be apparent from the description, or may be learned by practice of the presented exemplary embodiments.

According to one or more exemplary embodiments, a method of generating a body marker includes selecting a first body marker from among a plurality of prestored body markers based on an object shown in a medical image, generating a second body marker by modifying the first body marker according to a user input, and displaying the second body marker.

The second body marker may include a body marker generated by flipping the first body marker about a vertical axis.

The second body marker may include a body marker generated by rotating the first body marker about a central axis of the first body marker.

The second body marker may include a body marker generated by rotating the first body marker in a clockwise direction.

The second body marker may include a body marker generated by rotating the first body marker in a counterclockwise direction.

The selecting may include receiving a user input for selecting the first body marker that corresponds to the object from among a plurality of prestored body markers, and selecting the first body marker based on the received user input.

The selecting may include selecting a portion of the object shown in the medical image, and selecting the first body marker based on the selected portion of the object.

The plurality of prestored body markers may be sorted into application groups.

The first body marker and the second body marker may be 2-dimensional or 3-dimensional.

The user input may include a user gesture input on a touch screen.

The displaying may include displaying the first and second body markers on a single screen.

According to one or more exemplary embodiments, a non-transitory computer-readable recording medium having recorded thereon a program, which, when executed by a computer, performs the method above.

According to one or more exemplary embodiments, an apparatus for generating a body marker includes a display displaying a medical image showing an object, and a controller selecting a first body marker from among a plurality of prestored body markers based on the object, and generating a second body marker by modifying a shape of the first body marker according to a user input. The display displays the second body marker.

The second body marker may include a body marker generated by flipping the first body marker about a vertical axis.

The second body marker may include a body marker generated by flipping the first body marker about a horizontal axis.

The second body marker may include a body marker generated by rotating the first body marker in a clockwise direction.

The second body marker may include a body marker generated by rotating the first body marker in a counterclockwise direction.

The apparatus may further include an input unit receiving a user input for selecting the first body marker that corresponds to the object from among a plurality of prestored body markers, and the controller may select the first body marker based on the received user input.

The apparatus may further include an image processor selecting a portion of the object from the medical image, and the controller may select the first body marker based on the selected portion of the object.

The plurality of prestored body markers may be sorted into application groups.

The first body marker and the second body marker may be 2-dimensional or 3-dimensional.

The user input may include a user gesture input on a touch screen.

The display may display the first and second body markers on a single screen.

BRIEF DESCRIPTION OF THE DRAWINGS

Exemplary embodiments will now be described more fully hereinafter with reference to the accompanying drawings, in which reference numerals denote structural elements.

FIGS. 10A to 10D are diagrams illustrating another example of a controller generating a second body marker, according to an exemplary embodiment;

FIGS. 12A and 12B are diagrams illustrating another example of a controller generating a second body marker, according to an exemplary embodiment;

DETAILED DESCRIPTION

Figure 1:
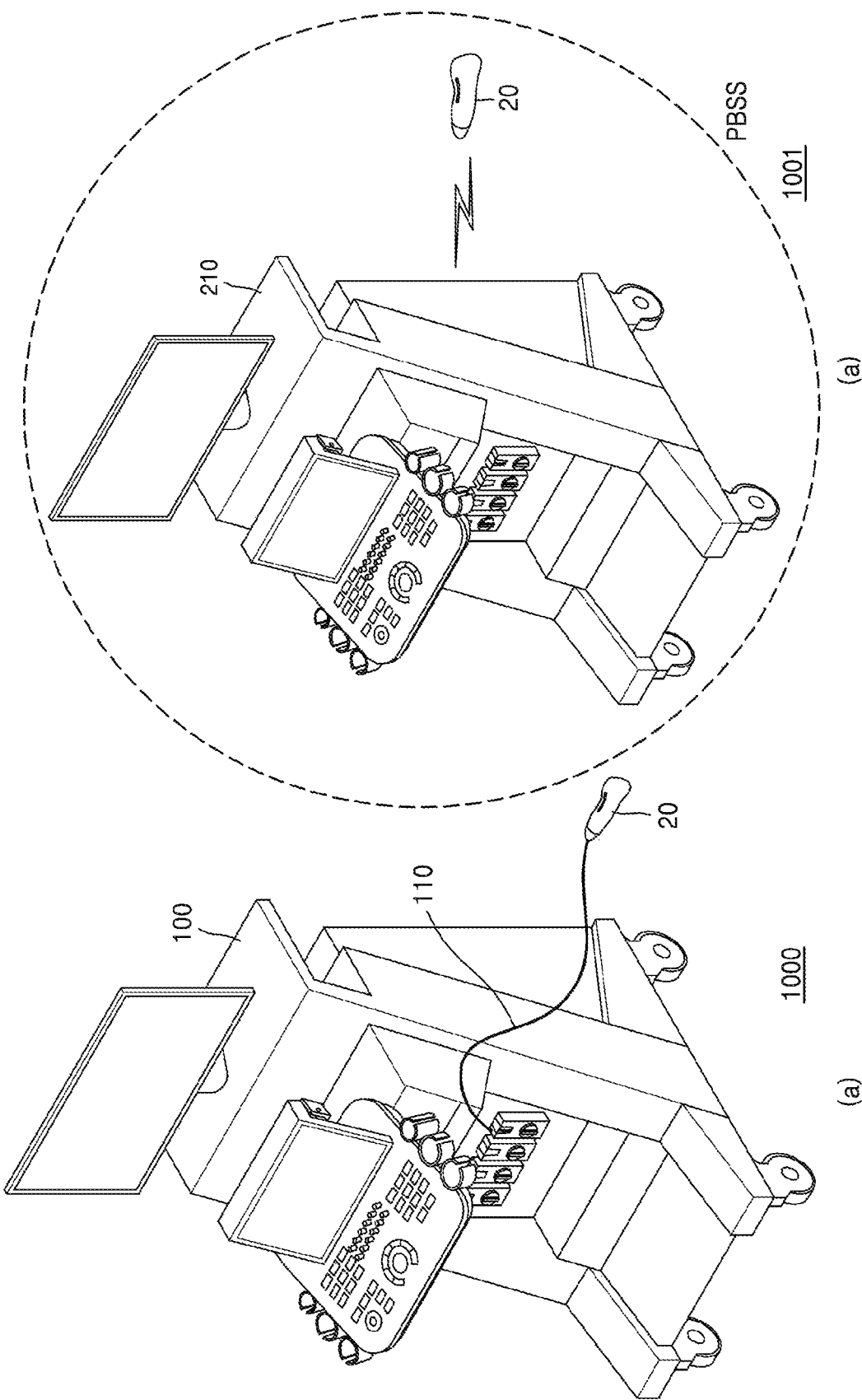
FIGS. 1A and 1B are diagrams illustrating an ultrasound diagnosis system according to an exemplary embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the inventive concept. As used herein, the term "and/or" includes any and all combinations of one or more of the associated listed items. Expressions such as "at least one of," when preceding a list of elements, modify the entire list of elements and do not modify the individual elements of the list.

Throughout the specification, it will also be understood that when a component "includes" an element, unless there is another opposite description thereto, it should be understood that the component does not exclude another element and may further include another element. In addition, terms such as " . . . unit," " . . . module," or the like refer to units that perform at least one function or operation, and the units may be implemented as hardware or software or as a combination of hardware and software.

Throughout the specification, an "ultrasound image" refers to an image of an object or an image of a region of interest included in the object, which is obtained using ultrasound waves. The region of interest is a region in the object which a user wants to focus on, for example, a lesion. Furthermore, an "object" may be a human, an animal, or a part of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Exemplary embodiments will now be described more fully hereinafter with reference to the accompanying drawings.

FIGS. 1A and 1B are diagrams illustrating an ultrasound diagnosis system 1000 according to an exemplary embodiment.

Referring to FIG. 1A, a probe 20 may be wired to an ultrasound imaging device 100 in the ultrasound diagnosis system 1000. In other words, the probe 20, which transmits and receives ultrasound, may be connected to a main body of the ultrasound diagnosis system 1000, i.e., the ultrasound image device 100, via a cable 110.

Referring to FIG. 1B, the probe 20 may be wirelessly connected to the ultrasound imaging device 100 in an ultrasound diagnosis system 1001. In other words, the probe 20 and the ultrasound imaging device 100 may be connected via a wireless network. For example, the probe 20 may be connected to the ultrasound imaging device 100 via a millimeter wave (mmWave) wireless network, receive an echo signal via a transducer, and transmit the echo signal in a 60 GHz frequency range to the ultrasound imaging device 100. Also, the ultrasound imaging device 100 may generate an ultrasound image of various modes by using the echo signal received in the 60 GHz frequency range, and display the generated ultrasound image. The millimeter wave wireless network may use, but is not limited to, a wireless communication method according to the Wireless Gigabit Alliance (WiGig) standard.

Figure 2:
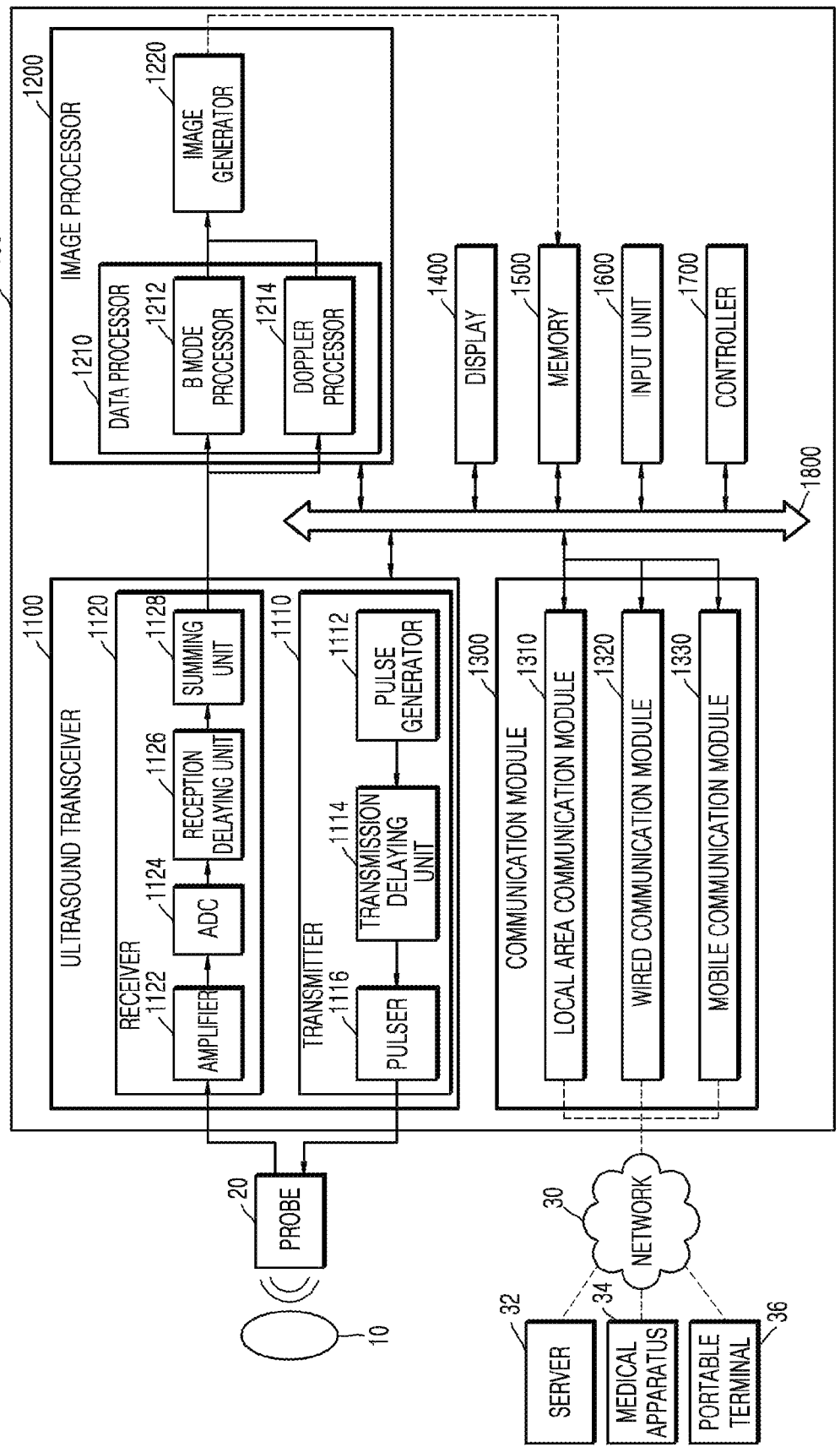
FIG. 2 is a block diagram illustrating an ultrasound diagnosis system according to an exemplary embodiment.

FIG. 2 is a block diagram illustrating an ultrasound diagnosis system 1002 according to an exemplary embodiment.

Referring to FIG. 2, the ultrasound diagnosis system 1002 may include a probe 20 and an ultrasound imaging device 100. Referring to FIG. 1, the ultrasound imaging device 100 may include an ultrasound transceiver 1100, an image processor 1200, a communication module 1300, a display 1400, a memory 1500, an input unit 1600, and a controller 1700, which may be connected to one another via buses 1800.

The ultrasound imaging device 1002 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 may transmit ultrasound waves to an object 10 (or, a region of interest in the object 10) in response to a driving signal applied by the ultrasound transceiver 1100 and receives echo signals reflected by the object 10 (or, the region of interest in the object 10). The probe 20 includes a plurality of transducers, and the plurality of transducers oscillate in response to electric signals and generate acoustic energy, that is, ultrasound waves. Furthermore, the probe 20 may be wired or wirelessly connected to a main body of the ultrasound diagnosis system 1002, and the ultrasound diagnosis system 1002 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning the object 10 in an amplitude (A) mode, a brightness (B) mode, and a motion (M) mode, but also a Doppler image showing a movement of the object 10 via a Doppler effect. The Doppler image may be a blood flow Doppler image showing flow of blood (also referred to as a color Doppler image), a tissue Doppler image showing a movement of tissue, or a spectral Doppler image showing a moving speed of the object 10 as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of the object 10 as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

Also, the image processor 1200 may select a portion of the object 10 shown in the ultrasound image.

The display 1400 displays the generated ultrasound image. The display 1400 may display not only an ultrasound image, but also various pieces of information processed by the ultrasound imaging device 1002 on a screen image via a graphical user interface (GUI). In addition, the ultrasound imaging device 100 may include two or more display 1400 according to embodiments.

Also, the display 1400 may display at least one body marker from among the body markers stored in the memory 1500, and the display 1400 may display a second body marker that is generated according to a user input.

The communication module 1300 is wired or wirelessly connected to a network 30 to communicate with an external device or a server. Also, when the probe 20 is connected to the ultrasound imaging device 100 via a wireless network, the communication module 1300 may communicate with the probe 20.

The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of the object 10, e.g., an ultrasound image, ultrasound data, and Doppler data of the object 10, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is wired to the network 30 or connected wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound imaging device 1000. For example, the memory 1500 may store medical data related to diagnosis of the object 10, such as ultrasound data and an ultrasound image that are input or output, and may also store algorithms or programs which are to be executed in the ultrasound imaging device 1002.

Also, the memory 1500 may store pre-generated body markers and a body marker generated by the controller 1700.

The memory 1500 may be any of various storage media, e.g., a flash memory, a hard disk drive, EEPROM, etc. Furthermore, the ultrasound imaging device 1002 may utilize web storage or a cloud server that performs the storage function of the memory 1500 online.

The input unit 1600 refers to a unit via which a user may input data for controlling the ultrasound imaging device 1002. The input unit 1600 may include hardware components, such as a keyboard, a mouse, a touch pad, a touch screen, and a jog switch, and a software module for driving the hardware components. However, the exemplary embodiments are not limited thereto, and the input unit 1600 may further include any of various input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

Also, the input unit 1600 may receive a user input for selecting a first body marker from among the body markers stored in the memory 1500.

The controller 1700 may control all operations of the ultrasound imaging device 1000. In other words, the controller 1700 may control operations among the probe 20, the ultrasound transceiver 1100, the image processor 1200, the communication module 1300, the display 1400, the memory 1500, and the input unit 1600 shown in FIG. 1.

The controller 1700 according to an exemplary embodiment may select a first body marker from among prestored body markers based on the object 10. The prestored body markers are the body markers that are preset and stored in the memory 1500, regardless of a shape or a location of the object 10 shown on the ultrasound image.

Also, the controller 1700 may generate a second body marker by reshaping or modifying an orientation of the first body marker according to a user input. The user input is input via the input unit 1600, and includes a gesture performed by the user, for example, tapping, touch and hold, double tapping, dragging, panning, flicking, drag and drop, pinching, and stretching.

For example, a first body marker may be selected from the body markers stored in the memory 1500 according to a user input received by the input unit 1600. An example of the first body marker being selected according to the user input will be described in detail with reference to FIGS. 15, 16A, and 16B. As another example, a first body marker may be selected from the body markers stored in the memory 1500 based on a portion of the object 10 selected from the ultrasound image by the image processor 1200. An example of the first body marker being selected based on the portion of the object 10 selected from the ultrasound image will be described in detail with reference to FIGS. 17, 18A, and 18B.

All or some of the probe 20, the ultrasound transceiver 1100, the image processor 1200, the communication module 1300, the display 1400, the memory 1500, the input unit 1600, and the controller 1700 may be implemented as software modules. Furthermore, at least one selected from the ultrasound transceiver 1100, the image processor 1200, and the communication module 1300 may be included in the controller 1700. However, the exemplary embodiments are not limited thereto.

Figure 3:
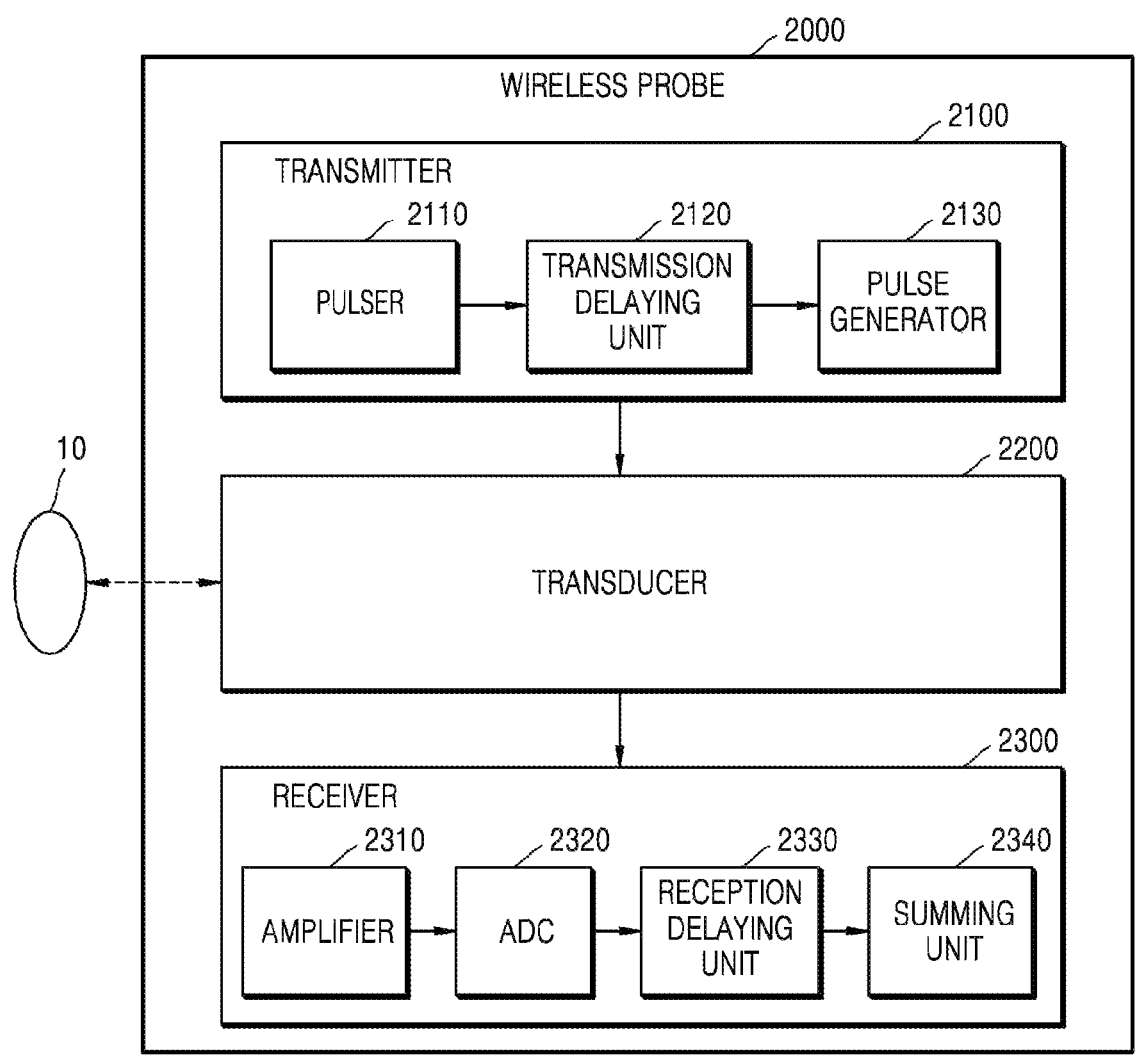
FIG. 3 is a block diagram illustrating a wireless probe according to an exemplary embodiment.

FIG. 3 is a block diagram illustrating a wireless probe 2000 according to an exemplary embodiment.

As described above with reference to FIG. 3, the wireless probe 2000 may include a plurality of transducers, and, according to embodiments, may include some or all of the components of the ultrasound transceiver 1100 shown in FIG. 2.

The wireless probe 2000 according to the embodiment shown in FIG. 3 includes a transmitter 2100, a transducer 2200, and a receiver 2300. Since descriptions thereof are given above with reference to FIG. 2, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis system 1002 shown in FIG. 2.

Figure 4:
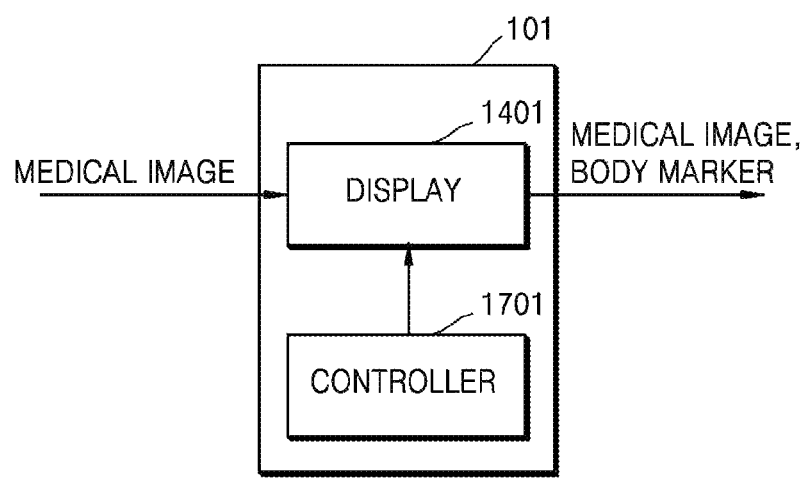
FIG. 4 is a block diagram illustrating an apparatus for generating a body marker, according to an exemplary embodiment.

FIG. 4 is a block diagram illustrating an apparatus 101 for generating a body marker, according to an exemplary embodiment.

Referring to FIG. 4, the apparatus 101 may include a controller 1701 and a display 1401. One or both of the controller 1701 and the display 1401 may be implemented as software modules, but are not limited thereto. One of the controller 1701 and the display 1401 may be implemented as hardware. Also, the display 1401 may include an independent control module.

Also, the controller 1701 may be the same as the controller 1700 of FIG. 2, and the display 1401 may be the same as the display 1400 of FIG. 2. If the apparatus 101 is a component included in an ultrasound imaging device, then, in addition to the controller 1701 and the display 1401, the apparatus 101 may further include the ultrasound transceiver

1100, the image processor 1200, the communication module 1300, the memory 1500, and the input unit 1600 shown in FIG. 2.

The controller 1701 may select a first body marker from prestored body markers based on an object shown in a medical image. The body markers may be stored in a memory (not shown) of the apparatus 101.

A body marker refers to a figure added to a medical image (e.g., an ultrasound image) so that a viewer of the medical image (e.g., a user) may easily recognize an object shown in the medical image.

The first body marker according to an exemplary embodiment refers to a body marker that is pre-generated and stored in the apparatus 101. That is, the first body marker refers to a body marker generated in advance by a manufacturer of the user, regardless of information of a current shape or location of the object shown in the medical image.

Since the first body marker does not reflect the current shape or the location of the object, when the first body marker is added to the medical image, the viewer of the medical image may be unable to accurately recognize the shape, position, or orientation of the object. Also, since the first body marker is selected from the prestored body markers, a large amount of time may be required for a user to select an appropriate body marker for the object. Hereinafter, the first body marker will be described in detail with reference to FIGS. 5A to 5C.

Figure 5A:
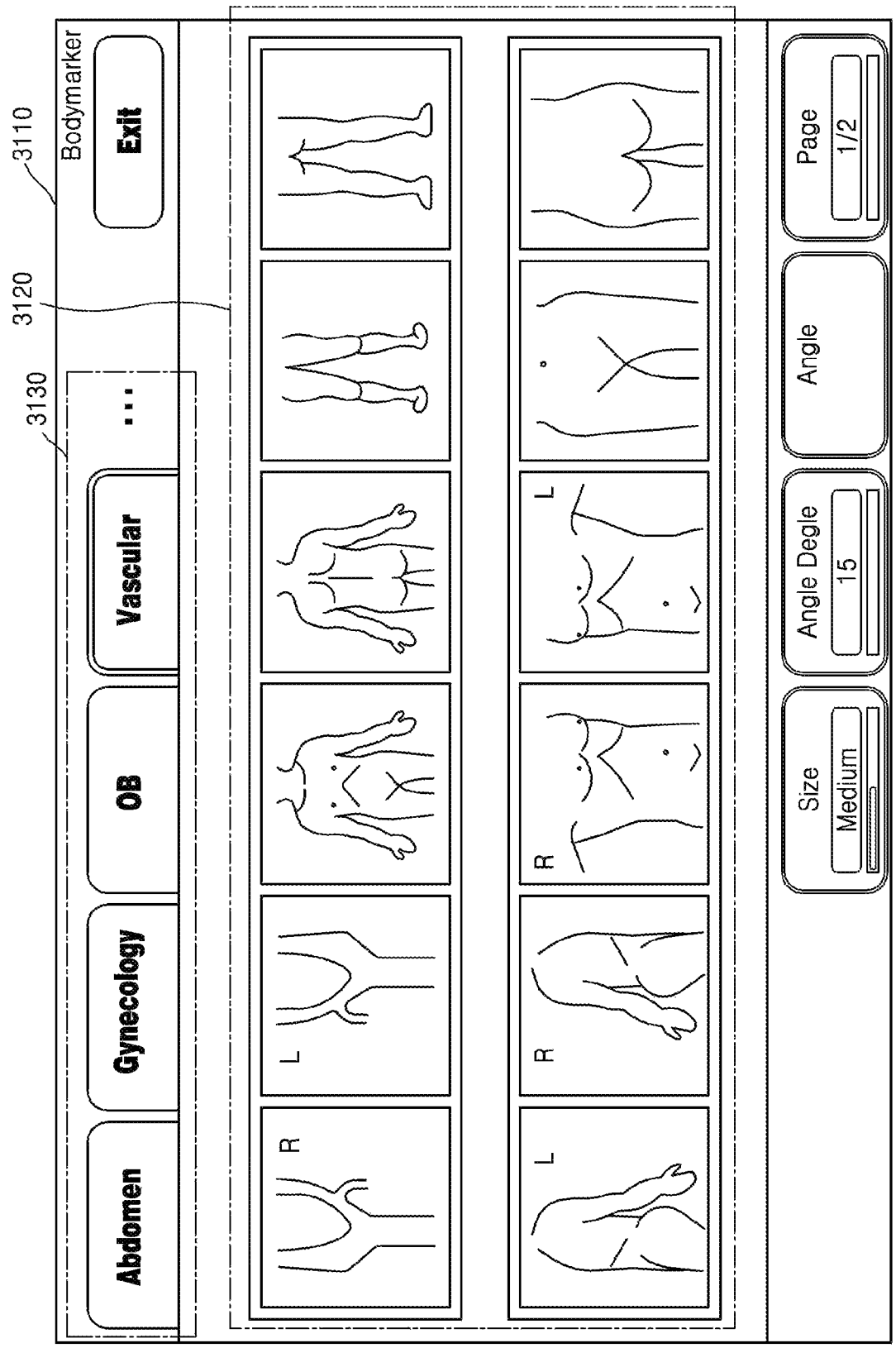
FIGS. 5A to 5C are diagrams illustrating a first body marker according to an exemplary embodiment.
Figure 5B:
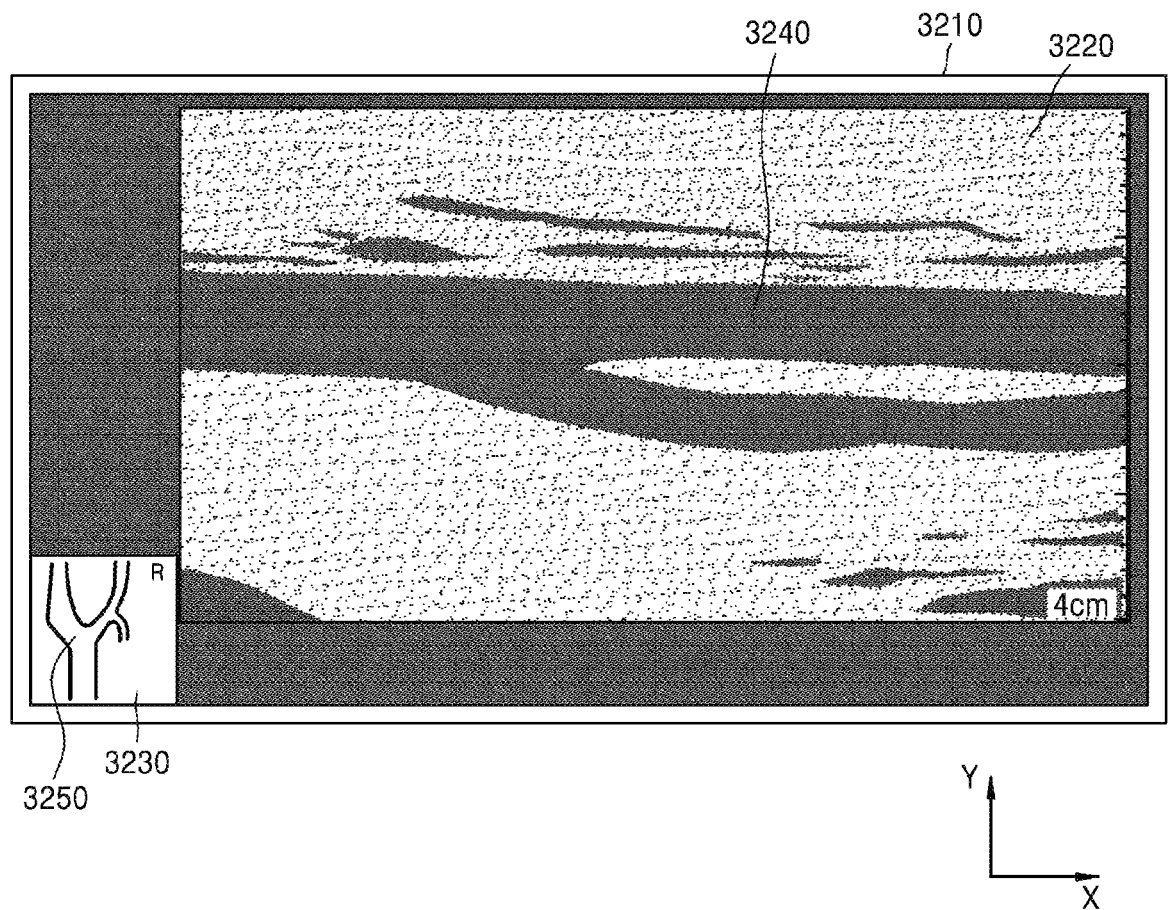
Figure 5C:
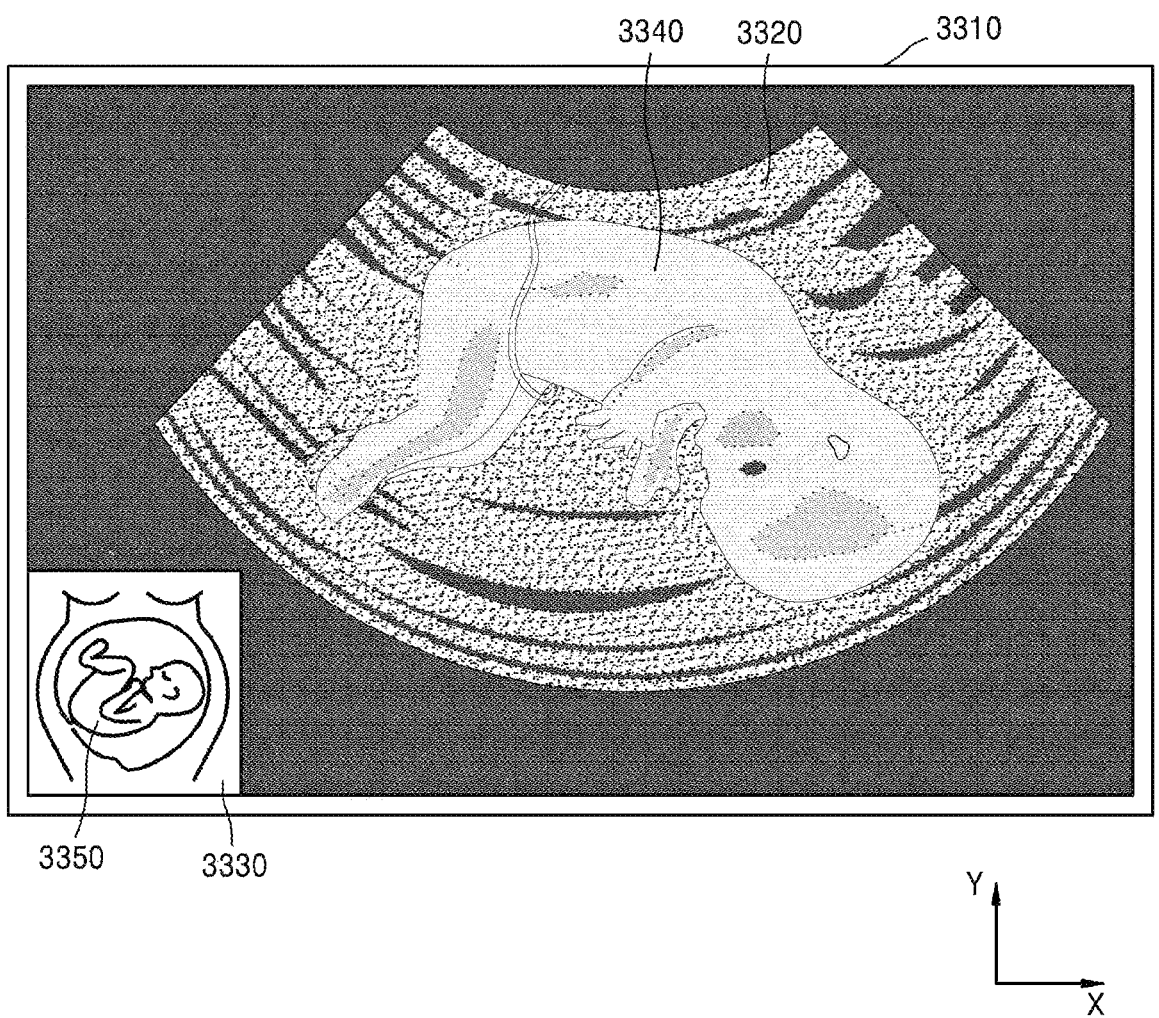

FIGS. 5A to 5C are diagrams illustrating a first body marker according to an exemplary embodiment.

Referring to FIG. 5A, a screen 3110 displays an example of prestored body markers 3120. The controller 1701 may select a first body marker from any one of the body markers 3120 based on an object shown in a medical image.

The body markers 3120 may be sorted into application groups 3130. An application refers to a diagnosis type determined based on a body part or an organ of a human or an animal.

For example, the application groups 3130 may include an abdomen group, a small part group including the chest, mouth, sexual organs, and the like, a vascular group, a musculoskeletal group, an obstetrics group, a gynecology group, a cardiac group, a brain group, a urology group, and a veterinary group. However, the application groups 3130 are not limited thereto. Body parts and organs of a human or an animal may be sorted into a plurality of application groups based on a predetermined standard.

The display 1401 may display the body markers 3120, which are sorted into the application groups 3130, on the screen 3110. For example, the user may select (e.g., click or tap) a 'Vascular' icon from icons representing the application groups 3130 displayed on the screen 3110. Then, from among the body markers 3120, the display 1401 may display body markers included in the vascular group on the screen 3110.

The body markers 3120 are generated and stored in advance. Accordingly, the user has to examine the body markers 3120 and select a first body marker that is the most appropriate for an object in a medical image. Therefore, it may require a large amount of time for the user to select the first body marker.

Also, the first body marker selected from the body markers 3120 may not include accurate information about the object. This will be described in detail with reference to FIG. 5B.

FIG. 5B illustrates an example of a medical image 3220 displayed on a screen 3210 and a first body marker 3230 added to the medical image 3220. For convenience of description, FIG. 5B is described assuming that the medical image 3220 is an ultrasound image showing a portion of blood vessels.

In order to facilitate understanding of a viewer of the medical image 3220, the first body marker 3230 may be added to the medical image 3220. The first body marker 3230 is selected from pre-generated body markers. Therefore, by viewing only the first body marker 3230, the viewer may only be able to recognize that the medical image 3220 obtained is a captured image of blood vessels, without knowing which portion of the blood vessels is shown in the medical image 3220.

The first body marker 3230 cannot be rotated or modified in any other manner. According to a direction of blood vessels 3250 shown in the first body marker 3230, the first body marker 3230 may be unable to accurately indicate a direction of blood vessels 3240 shown in the medical image 3220. For example, referring to FIG. 5B, the blood vessels 3240 in the medical image 3220 are oriented with respect to an x-axis, whereas the blood vessels 3250 in the first body marker 3230 are oriented with respect to a y-axis. Therefore, the first body marker 3230 does provide accurate information about the object.

FIG. 5C illustrates an example of a medical image 3320 displayed on a screen 3310 and a first body marker 3330 added to the medical image 3320. For convenience of description, FIG. 5C is described assuming that the medical image 3320 is an ultrasound image showing a fetus.

A fetus 3340 of the ultrasound image 3320 is shown lying parallel to the x-axis and facing downward. However, a fetus 3350 of the first body marker 3330 is shown lying parallel to the x-axis and facing upward. Therefore, the first body marker 3330 does not provide accurate information about the fetus 3340 shown in the ultrasound image 3320.

As described above with reference to FIGS. 5A to 5C, the first body marker, which is a pre-generated body marker, may not accurately represent an object included in a medical image.

The controller 1701 according to an exemplary embodiment may generate a second body marker by modify a shape, orientations, or positions of the first body marker. Therefore, the controller 1701 may generate a body marker that accurately shows information about an object. Hereinafter, the second body marker will be described in detail with reference to FIG. 6.

Figure 6:
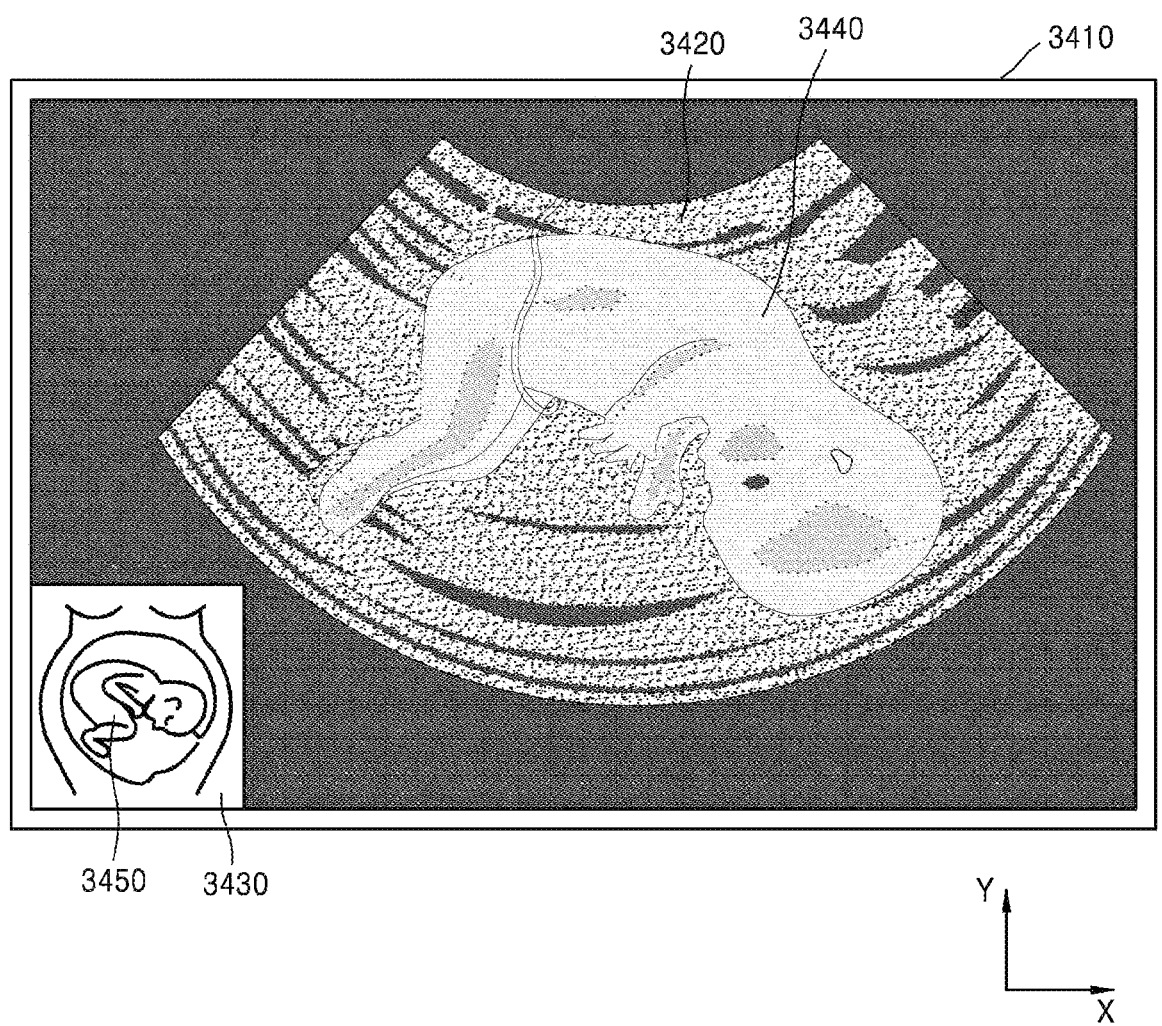
FIG. 6 is a diagram illustrating a second body marker according to an exemplary embodiment.

FIG. 6 is a diagram illustrating a second body marker 3430 according to an exemplary embodiment.

FIG. 6 illustrates an example of a medical image 3420 displayed on a screen 3410 and a second body marker 3430 added to the medical image 3420. For convenience of description, FIG. 6 is described assuming that the medical image 3320 is an ultrasound image showing a fetus.

A fetus 3440 of the ultrasound image 3420 is shown lying parallel to the x-axis and facing downward. A fetus 3450 of the second body marker 3430 is also shown lying parallel to the x-axis and facing downward. In other words, the second body marker 3430 accurately shows an orientation and a facing direction of the fetus 3440 of the ultrasound image 3420.

As described above with reference to FIG. 5C, the first body marker 3330 does not accurately show a facing direction of the fetus 3340 of the ultrasound image 3320. Therefore, the viewer may be unable to obtain accurate information about the fetus 3340 shown in the ultrasound image 3320 based on only the first body marker 3330. However, as shown in FIG. 6, the second body marker 3430 accurately shows the orientation and location of the fetus 3440 of the ultrasound image 3420, and thus, the viewer may obtain accurate information about the fetus 3440 shown in the ultrasound image 3420 based on only the second body marker 3430.

Referring back to FIG. 4, the controller 1701 may generate a second body marker by changing a shape of a first body marker according to a user input. For example, the controller 1701 may modify the shape, orientations, or positions of the first body marker according to a user input received via an input unit (not shown) in the apparatus 101. The input unit in the apparatus 101 may be the same as the input unit 1600 described with reference to FIG. 2.

For example, in the case that the input unit includes hardware components, such as a keyboard, a mouse, a trackball, and a jog switch, and a software module for driving the hardware components, the user input may include clicking a predetermined point on a screen or inputting a drag gesture from a point on the screen to another point on the screen. As another example, in the case that the input unit includes a touch screen and a software module for driving the touch screen, the user input may include a user gesture input on the touch screen. The gesture may include, for example, tapping, touch and hold, double tapping, dragging, scrolling, flicking, drag and drop, pinching, and stretching.

For example, the controller 1701 may generate a second body marker by flipping the first body marker about a vertical axis according to the user input. As another example, the controller 1701 may generate a second body marker by rotating the first body marker about a central axis of the first body marker according to the user input. As another example, the controller 1701 may generate a second body marker by rotating the first body marker in a clockwise or counterclockwise direction according to the user input.

The display 1401 may display a medical image showing an object on a screen. Also, the display 1401 may display the second body marker generated by the controller 1701 on the screen. The display 1401 may display the first body marker and the second body marker on a single screen.

The controller 1701 may generate the second body marker by changing the shape of the first body marker according to the user input. In order to help the user to accurately input data, the display 1401 may display the first body marker and a predetermined guide image on the screen. Hereinafter, the first body marker and the predetermined guide image displayed by the display 1401 will be described in detail with reference to FIGS. 7A and 7B.

Figure 7A:
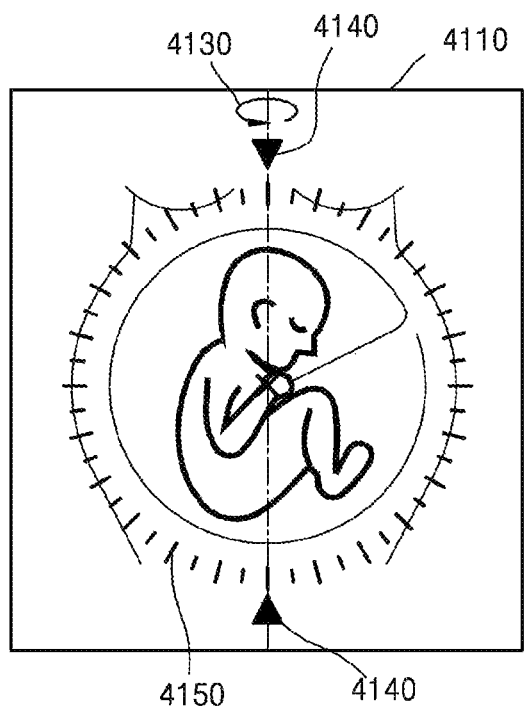
FIGS. 7A and 7B are diagrams illustrating images used for generating a second body marker, according to an exemplary embodiment.
Figure 7B:
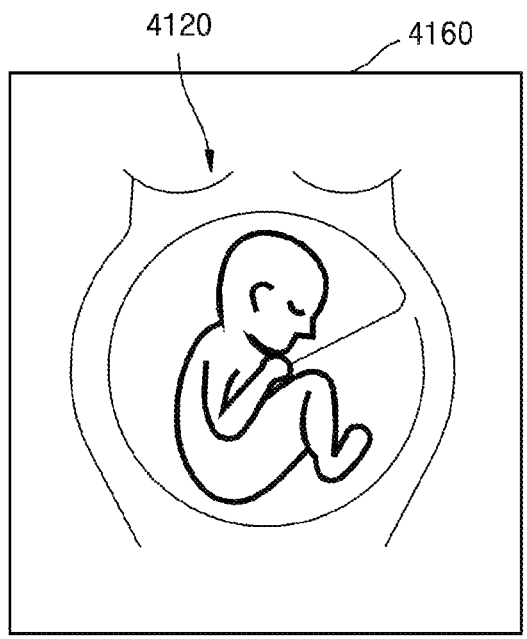

FIGS. 7A and 7B are diagrams illustrating images used for generating a second body marker, according to an exemplary embodiment.

FIG. 7A illustrates an example of a first body marker 4120 and first to third guide images 4130, 4140, and 4150 displayed on a screen 4110. The user may provide a user input to the apparatus 101 based on the first body marker 4120 and the first to third guide images 4130, 4140, and 4150 displayed on the screen 4110.

The user may select a point on the guide images 4130, 4140, and 4150 according to a predetermine rule, or input a drag gesture beginning from a point on the guide images 4130, 4140, and 4150 to another point thereon. Also, the controller 1701 may modify a shape, orientations, or positions of the first body marker 4120 according to the user input.

For convenience of description, the user input is assumed as a gesture performed by the user in FIGS. 7A to 14B. However, the user input is not limited thereto. As described above, the user may provide the user input to the apparatus 101 by using various hardware components, such as a keyboard or a mouse.

For example, when the user taps the first guide image 4130 or inputs a drag gesture along points surrounding the first guide image 4130 in a clockwise or counterclockwise direction, the controller 1701 may rotate a portion of the first body marker 4120 about the central axis thereof.

As another example, when the user taps the second guide image 4140, the controller 1701 may rotate a portion of the first body marker 4120 toward the second guide image 4140.

As another example, when the user taps the third guide image 4150 or inputs a drag gesture in a clockwise or counterclockwise direction along points surrounding the third guide image 4150, the controller 1701 may rotate a portion of the first body marker 4120 in a clockwise or counterclockwise direction.

Alternatively, as shown in FIG. 7B, only the first body marker 4120 may be displayed on a screen 4160. In other words, the first to third guide images 4130, 4140, and 4150 of FIG. 7A may be omitted from the screen 4160. In the case of FIG. 7B, the user may also provide the user input, as described above with reference to FIG. 7A, to the apparatus 101, and the controller 1701 may modify a shape, orientations, or positions of the first body marker 4120 according to the user input.

Hereinafter, examples of the controller 1701 generating a second body marker by modifying a shape of a first body marker will be described in detail with reference to FIGS. 8A to 14B. In FIGS. 8A to 14B, it is assumed that the guide images 4130, 4140, and 4150 are not displayed on a screen.

Figure 8A:
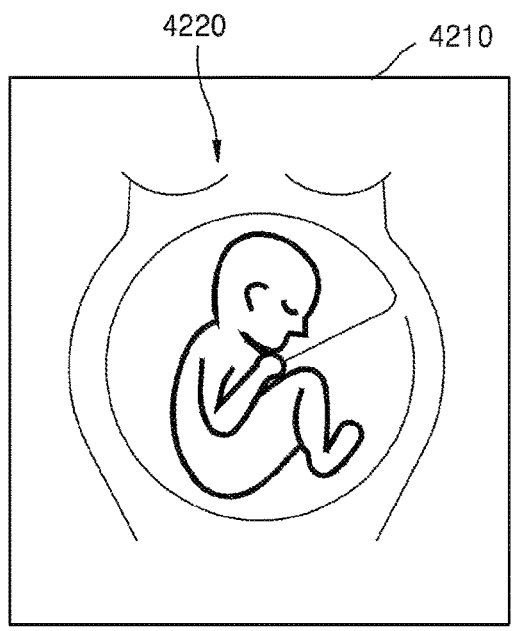
FIGS. 8A and 8B are diagrams illustrating an example of a controller generating a second body marker, according to an exemplary embodiment.
Figure 8B:
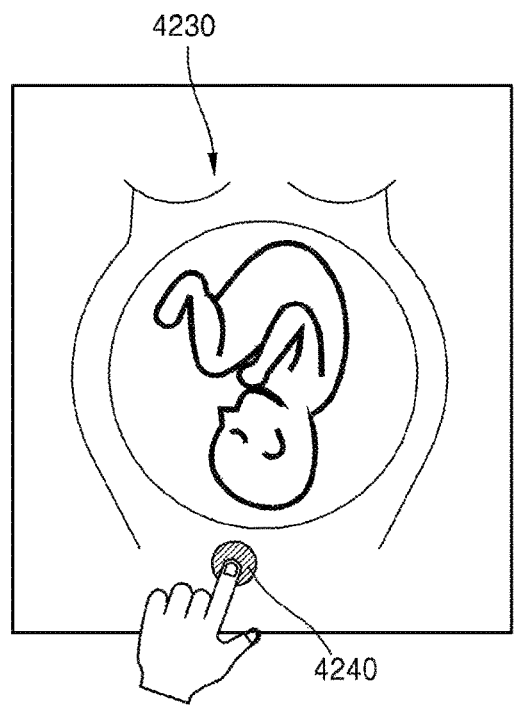

FIGS. 8A and 8B are diagrams illustrating an example of the controller 1701 generating a second body marker, according to an exemplary embodiment.

For example, the controller 1701 may generate a second body marker 4230 by rotating a portion of a first body marker 4220 according to a user input.

FIG. 8A illustrates an example of a screen 4210 displaying the first body marker 4220. The user may select (e.g., tap) an outer point of the first body marker 4220, and the controller 1701 may rotate the portion of the first body marker 4220 to the point selected by the user.

FIG. 8B illustrates an example of the second body marker 4230 generated by rotating the portion of the first body marker 4220. For example, when the first body marker 4220 represents a fetus, the controller 1701 may rotate the portion of the first body marker 4220 such that the head of the fetus is located toward a point 4240 selected by the user. In this case, the controller 1701 may rotate the portion of the first body marker 4220 in a clockwise or counterclockwise direction.

According to a rotation degree of a portion of the second body marker 4230, the second body marker 4230 may be the same as when the first body marker 4220 is flipped about a horizontal axis.

Accordingly, the controller 1701 may generate the second body marker 4230 by rotating the portion of the first body marker 4220 toward the point 4240 selected by the user. Also, the controller 1701 may store the second body marker 4230 in the memory of the apparatus 101.

Figure 9A:
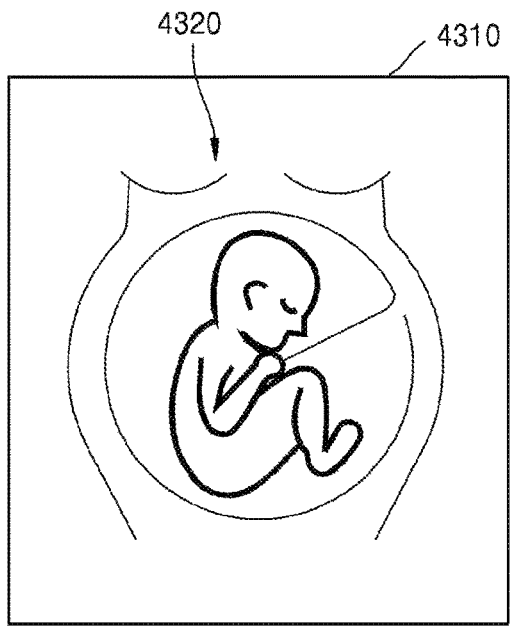
FIGS. 9A and 9B are diagrams illustrating another example of a controller generating a second body marker, according to an exemplary embodiment.
Figure 9B:
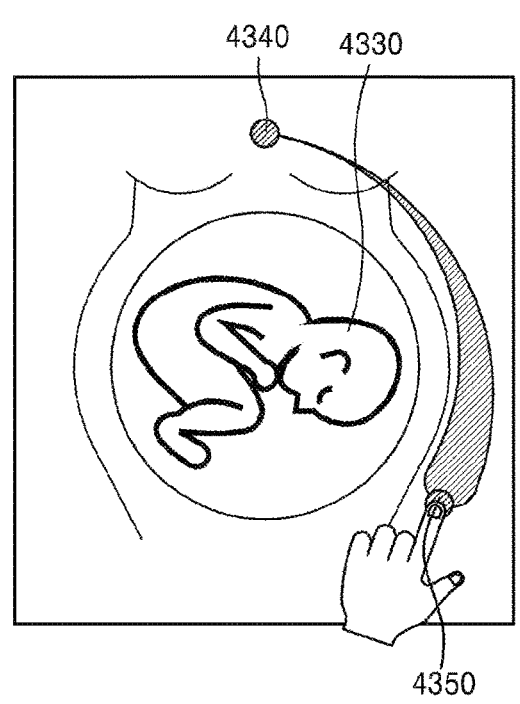

FIGS. 9A and 9B are diagrams illustrating another example of the controller 1701 generating a second body marker, according to an exemplary embodiment.

For example, the controller 1701 may generate a second body marker 4330 by rotating a portion of a first body marker 4320 in a clockwise or counterclockwise direction according to a user input.

FIG. 9A illustrates an example of a screen 4310 displaying the first body marker 4320. The user may input a drag gesture from an outer point on the first body marker 4320 to another outer point thereon in a clockwise or counterclockwise direction, and the controller 1701 may rotate the portion of the first body marker 4320 in a clockwise or counterclockwise direction according to the drag gesture input by the user.

FIG. 9B illustrates the second body marker 4330 generated by rotating the portion of the first body marker 4320 in a clockwise direction. For example, it is assumed that the first body marker 4320 represents a fetus, and the user inputs a drag gesture in a clockwise direction from a point 4340 toward which the head of the fetus 4833 is directed to another point 4350 on the first body marker 4320. In this case, the controller 1701 may rotate the portion of the first body marker 4320 in a clockwise direction such that the head of the fetus is pointed toward the point 4350 where the drag gesture stops.

Accordingly, the controller 1701 may generate the second body marker 4330 by rotating the portion of the first body marker 4320 in a clockwise direction toward the point 4350 selected by the user. Also, the controller 1701 may store the second body marker 4330 in the memory of the apparatus 101.

As described above with reference to FIGS. 9A to 9B, the controller 1701 may generate the second body marker 4330 by rotating the portion of the first body marker 4320 in a clockwise direction. However, when the user inputs a drag gesture in a counterclockwise direction, the controller 1701 may generate a second body marker by rotating a first body marker in a counterclockwise direction toward a point where the drag gesture stops.

FIGS. 10A to 10D are diagrams illustrating another example of the controller 1701 generating a second body marker, according to an exemplary embodiment.

For example, the controller 1701 may generate second body markers 4440, 4450, and 4460 by rotating a portion of a first body marker 4420 about a central axis of the first body marker 4420 according to a user input.

FIG. 10A illustrates an example of a screen 4410 displaying the first body marker 4420. The user may select (e.g., tap) a point 4430 through which the central axis of the first body marker 4420 passes, and the controller 1701 may rotate the portion of the first body marker 4420 about the central axis thereof according to the selected point.

Although FIGS. 10B to 10D illustrate that the first body marker 4420 is rotated about the central axis thereof in a counterclockwise direction, the exemplary embodiments are not limited thereto. In other words, the controller 1701 may rotate the portion of the first body marker 4420 about the central axis thereof in the counterclockwise direction based on a predetermined rule.

FIG. 10B illustrates an example of the second body marker 4440 generated by rotating the portion of the first body marker 4420 by 90° about the central axis thereof. For example, it is assumed that the first body marker 4420 represents the fetus, when the user taps the point 4430 through which the central axis of the first body marker 4320 passes. In this case, the controller 1701 may rotate the portion of the first body marker 4320 by 90° about the central axis thereof in a counterclockwise direction.

FIG. 10C illustrates an example of the second body marker 4450 generated by rotating the portion of the second body marker 4440 of the FIG. 10B by 90° about a central axis of the second body marker 4440. For example, it is assumed that the second body marker 4440 represents the fetus, and the user taps the point 4430 through which the central axis of the second body marker 4440 passes. In this case, the controller 1701 may rotate the portion of the second body marker 4440 by 90° about the central axis thereof in a counterclockwise direction.

FIG. 10D illustrates an example of the second body marker 4460 generated by rotating the portion of the second body marker 4450 of FIG. 10C by 90° about a central axis of the second body marker 4450. For example, it is assumed that the second body marker 4450 represents the fetus, and the user taps the point 4430 through which the central axis of the second body marker 4450 passes. In this case, the controller 1701 may rotate the portion of the second body marker 4450 by 90° about the central axis thereof in a counterclockwise direction.

Accordingly, the controller 1701 may generate the second body markers 4440, 4450, and 4460 by rotating the portion of the first body marker 4420 about the central axis thereof. Also, the controller 1701 may store the second body markers 4440, 4450, and 4460 in the memory of the apparatus 101.

As described above with reference to FIGS. FIG. 10A to FIG. 10D, the controller 1701 may rotate the portion of the first body marker 4420 about the central axis thereof according to taps performed by the user. The taps may be continuous or discontinuous, but are not limited thereto.

For example, it is assumed that the user inputs a drag gesture in a clockwise direction from a point on the first body marker 4420 where the central axis of the first body marker 4420 passes through to another point on the first body marker 4420. Based on a distance of the drag gesture, the controller 1701 may rotate the first body marker 4420 about the central axis thereof in a clockwise direction. For example, when the user inputs a drag gesture in a clockwise direction from a first point to a second point, in which the distance between the first point and the second point is 1 mm, the controller 1701 may rotate the first body marker 4420 by 20° in a clockwise direction. However, the exemplary embodiments are not limited thereto. The distance of the drag gesture and a rotation degree of the first body marker 4420 may vary.

Figure 11A:
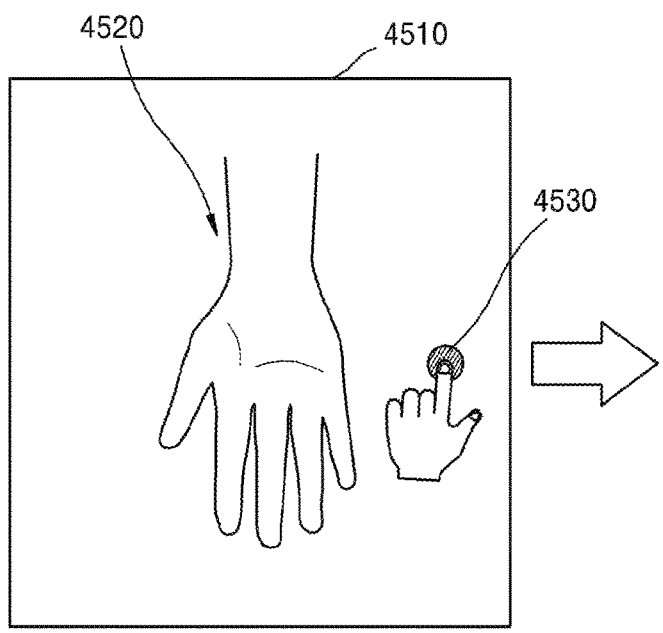
FIGS. 11A and 11B are diagrams illustrating another example of a controller generating a second body marker, according to an exemplary embodiment.
Figure 11B:
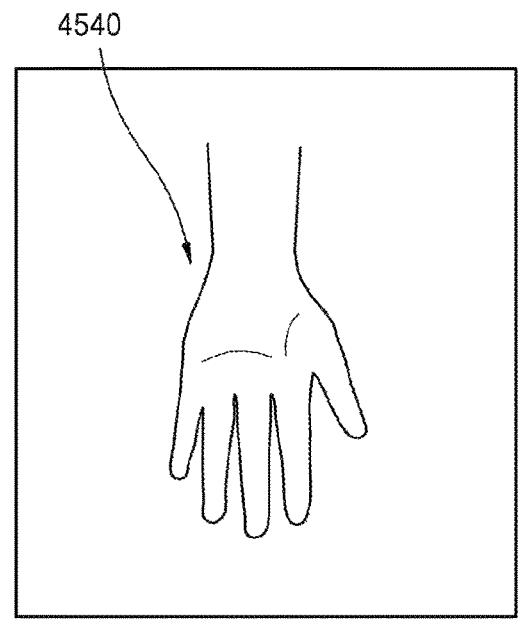

FIGS. 11A and 11B are diagrams illustrating another example of the controller 1701 generating a second body marker, according to an exemplary embodiment.

For example, the controller 1701 may generate a second body marker 4540 by flipping a first body marker 4520 about the vertical axis according to a user input.

FIG. 11A illustrates an example of a screen 4510 displaying the first body marker 4520. When the user selects (e.g., tap) an outer point 4530 on the first body marker 4520, the controller 1701 may flip the first body marker 4520 about the vertical axis.

FIG. 11B illustrates an example of the second body marker 4540 generated by flipping the first body marker 4520 about the vertical axis. For example, when the first body marker 4520 represents the palm of the right hand of a subject, the controller 1701 may flip the first body marker 4520 about the vertical axis to show an inverse image of the palm of the right hand.

Accordingly, the controller 1701 may generate the second body marker 4540 by flipping the first body marker 4520 about the vertical axis. Also, the controller 1701 may store the second body marker 4540 in the memory of the apparatus 101.

FIGS. 12A and 12B are diagrams illustrating another example of the controller 1701 generating a second body marker, according to an exemplary embodiment.

For example, the controller 1701 may generate a second body marker 4640 by flipping over a first body marker 4620 (i.e., rotating the first body marker 4620 by 180° about a central axis thereof in a clockwise or counterclockwise direction) according to a user input.

FIG. 12A illustrates an example of a screen 4610 displaying the first body marker 4620. When the user selects (e.g., tap) a point 4630 through which a central axis of the first body marker 4620 passes, the controller 1701 may flip over the first body marker 4620.

FIG. 12B illustrates an example of the second body marker 4640 generated by flipping over the first body marker 4620. For example, when the first body marker 4620 represents the palm of the right hand, the controller 1701 may flip over the first body marker 4620 to display the back of the right hand.

Accordingly, the controller 1701 may generate the second body marker 4640 by flipping over the first body marker 4620. Also, the controller 1701 may store the second body marker 4640 in the memory of the apparatus 101.

As described above with reference to FIGS. 8A to 12B, the controller 1701 may generate a second body marker that represents a single object by using a first body marker that represents a single object. However, a body marker may represent a plurality of objects. For example, when a medical image is obtained by capturing the uterus of a pregnant woman having twins, a body marker added to the medical image has to represent the twins (that is, a plurality of objects).

The controller 1701 according to an exemplary embodiment may generate a second body marker that represents a plurality of objects by using a first body marker that represents a single object. Hereinafter, examples of the controller 1701 generating a second body marker that represents a plurality of objects will be described with reference to FIGS. 13A to 14B.

Figure 13A:
FIGS. 13A and 13B are diagrams illustrating another example of a controller generating a second body marker, according to an exemplary embodiment.
Figure 13B:
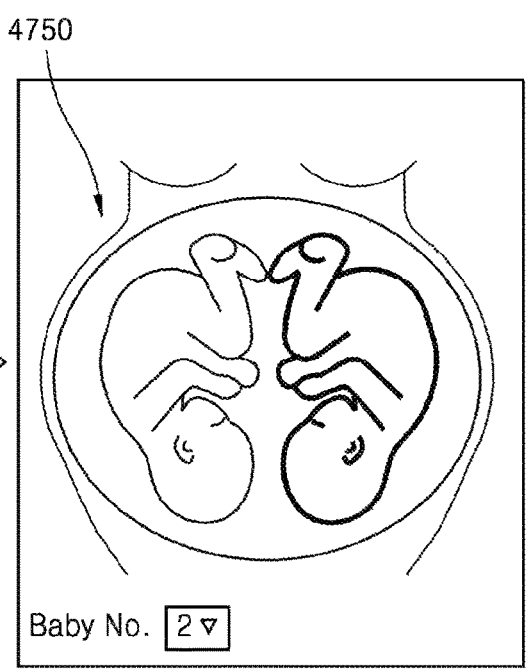

FIGS. 13A and 13B are diagrams illustrating another example of the controller 1701 generating a second body marker, according to an exemplary embodiment.

FIG. 13A illustrates an example of a screen 4710 displaying a first body marker 4720 that represents a single object. For convenience of description, it is assumed that the first body marker 4720 represents a fetus.

The controller 1701 may change the number of objects represented by a body marker, according to a user input. For example, when the user selects (e.g., taps) an icon 4730 displayed at a predetermined location on the screen 4710, the display 1401 may display a pop-up window 4740 showing the number of objects that may be represented by a body marker. Accordingly, the user may set the number of objects to be represented by the body marker.

When the user has set the body marker to represent 2 objects, the controller 1701 may generate a second body marker 4750 that includes 2 fetuses, as shown in FIG. 13B. Also, the controller 1701 may store the second body marker 4750 in the memory of the apparatus 101.

The controller 1701 may modify shapes, orientations, or positions of a plurality of objects included in a body marker. For example, when a medical image is obtained by capturing the uterus of a pregnant woman having twins, each fetus may be oriented in different directions. Therefore, the controller 1701 may modify the shape, orientations, or positions of the plurality of objects in the body marker to thus generate a body marker that accurately shows information about the objects.

Hereinafter, an example of the controller 1701 generating a second body marker by modifying the shape, orientations, or positions according to a plurality of objects included in a body marker will be described with reference to FIGS. 14A and 14B.

Figure 14A:
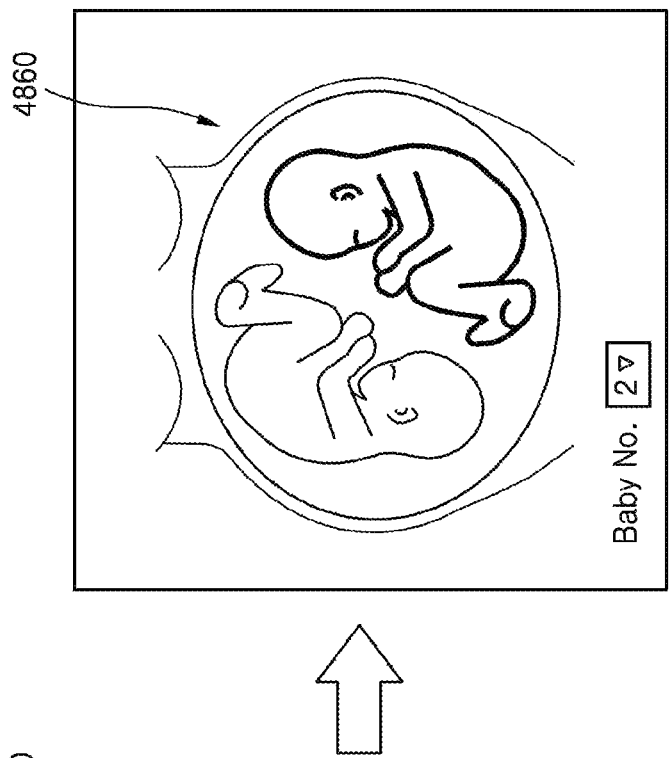
FIGS. 14A and 14B are diagrams illustrating another example of a controller generating a second body marker, according to an exemplary embodiment.
Figure 14B:
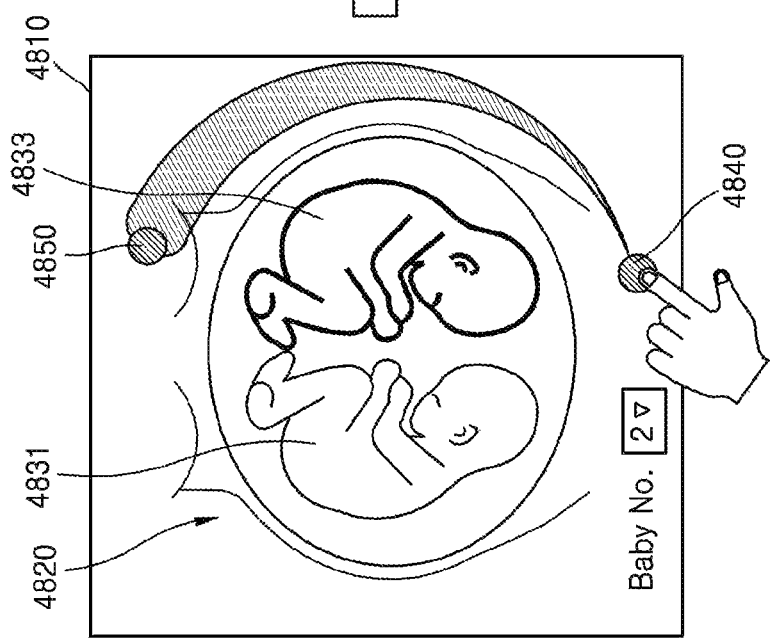

FIGS. 14A and 14B are diagrams illustrating another example of the controller 1701 generating a second body marker, according to an exemplary embodiment.

FIG. 14A illustrates an example of a screen 4810 displaying a first body marker 4820 that includes a plurality of objects. For convenience of description, it is assumed that the first body marker 4820 includes twins. Also, as described above with reference to FIGS. 13A and 13B, the controller 1701 may generate the first body marker 4820 by using a body marker that includes a single fetus.

Based on a user input, the controller 1701 may select an object from among objects included in a body marker. For example, when the user selects (e.g., taps) a fetus 4833 from fetuses 4831 and 4833 displayed on the screen 4810, the controller 1701 may determine the fetus 4833 as an object to be reshaped, reoriented, or repositioned. In this case, the display 1401 may display the fetuses 4831 and 4833 such that the fetus 4833 that is selected is distinguished from the fetus 4831 that is not selected (for example, change in thickness or line color). Thus, the user may easily recognize the selected fetus 4833.

The controller 1701 may modify a shape, orientations, or positions of the fetus 4833 according to a user input. The user input is the same as described above with reference to FIGS. 8A to 12B. For example, it is assumed that the user inputs a drag gesture in a clockwise direction from a point 4840 toward which the head of the fetus 4833 is directed to another point 4850. In this case, the controller 1701 may rotate the fetus 4833 such that the head is directed toward the point 4850 where the drag gesture stops.

Referring to FIG. 14B, the controller 1701 may generate a second body marker 4860 in which a location of the fetus 4833 of FIG. 14A is modified. Also, the controller 1701 may store the second body marker 4860 in the memory of the apparatus 101.

Although second body markers described above with reference to FIGS. 7A to 14B are 2-dimensional, the exemplary embodiments are not limited thereto. In other words, the controller 1701 may generate a 3-dimensional second body marker.

Figure 15:
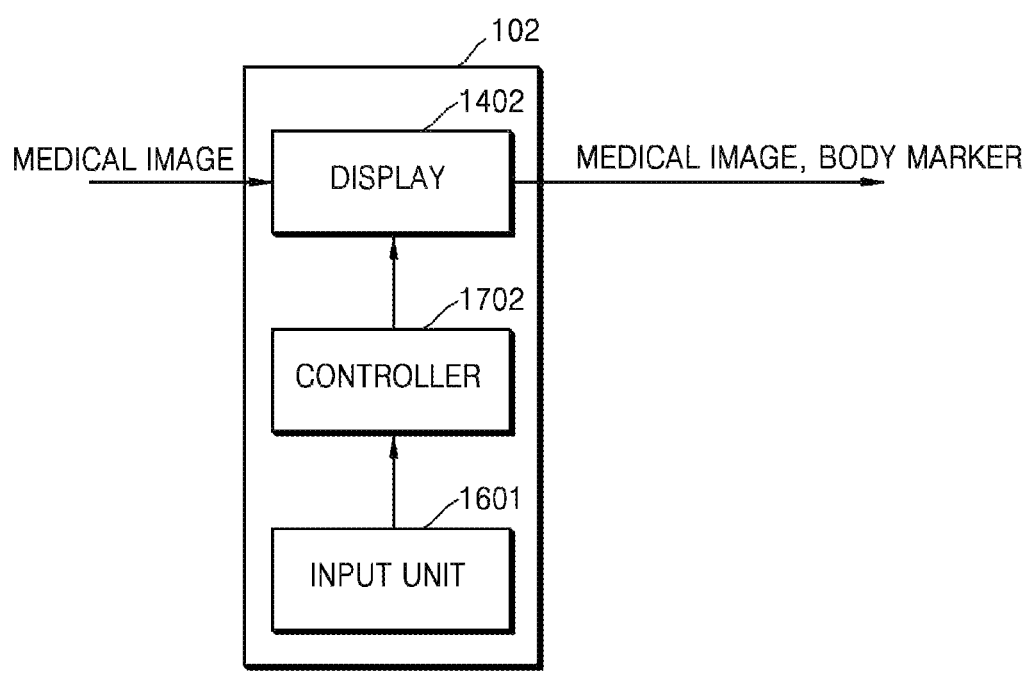
FIG. 15 is a block diagram illustrating an apparatus for generating a body marker, according to another exemplary embodiment.

FIG. 15 is a block diagram illustrating an apparatus 102 for generating a body marker, according to another exemplary embodiment.

Referring to FIG. 15, the apparatus 102 may include a controller 1702, a display 1402, and an input unit 1601. All or some of the controller 1702, the display 1402, and the input unit 1601 may be implemented as software modules, but are not limited thereto. Some of the controller 1702, the display 1402, and the input unit 1601 may be implemented as hardware. Also, each of the display 1402 and the input unit 1601 may include an independent control module.

Also, the controller 1702 may be the same as the controller 1701 of FIG. 4, the display 1402 may be the same as the display 1401 of FIG. 4, and the input unit 1601 may be the same as the input unit 1600 of FIG. 2. If the apparatus 102 is a component included in an ultrasound imaging device, then, in addition to the controller 1702, the display 1402, and the input unit 1601, the apparatus 102 may further include the ultrasound transceiver 1100, the image processor 1200, the communication module 1300, and the memory 1500 shown in FIG. 2.

Operations of the display 1402 are the same as operations of corresponding components described above with reference to FIGS. 4 to 14B. Therefore, detailed description of the display 1402 will not be repeated.

The input unit 1601 may receive a user input for selecting a first body marker corresponding to an object in a medical image. The user input refers to an input selecting the first body marker from prestored body markers.

The controller 1702 may select the first body marker based on the user input transmitted from the input unit 1601. Also, the controller 1702 may generate a second body marker by changing a shape of the first body marker according to a user input received after the user input for selecting the first body marker. Since examples of the controller 1702 generating the second body marker have been described above in detail with reference to FIGS. 8A to 14B, descriptions of the examples will not be repeated.

Hereinafter, an example of the input unit 1601 receiving a user input and the controller 1702 selecting a first body marker will be described in detail with reference to FIGS. 16A and 16B.

Figure 16A:
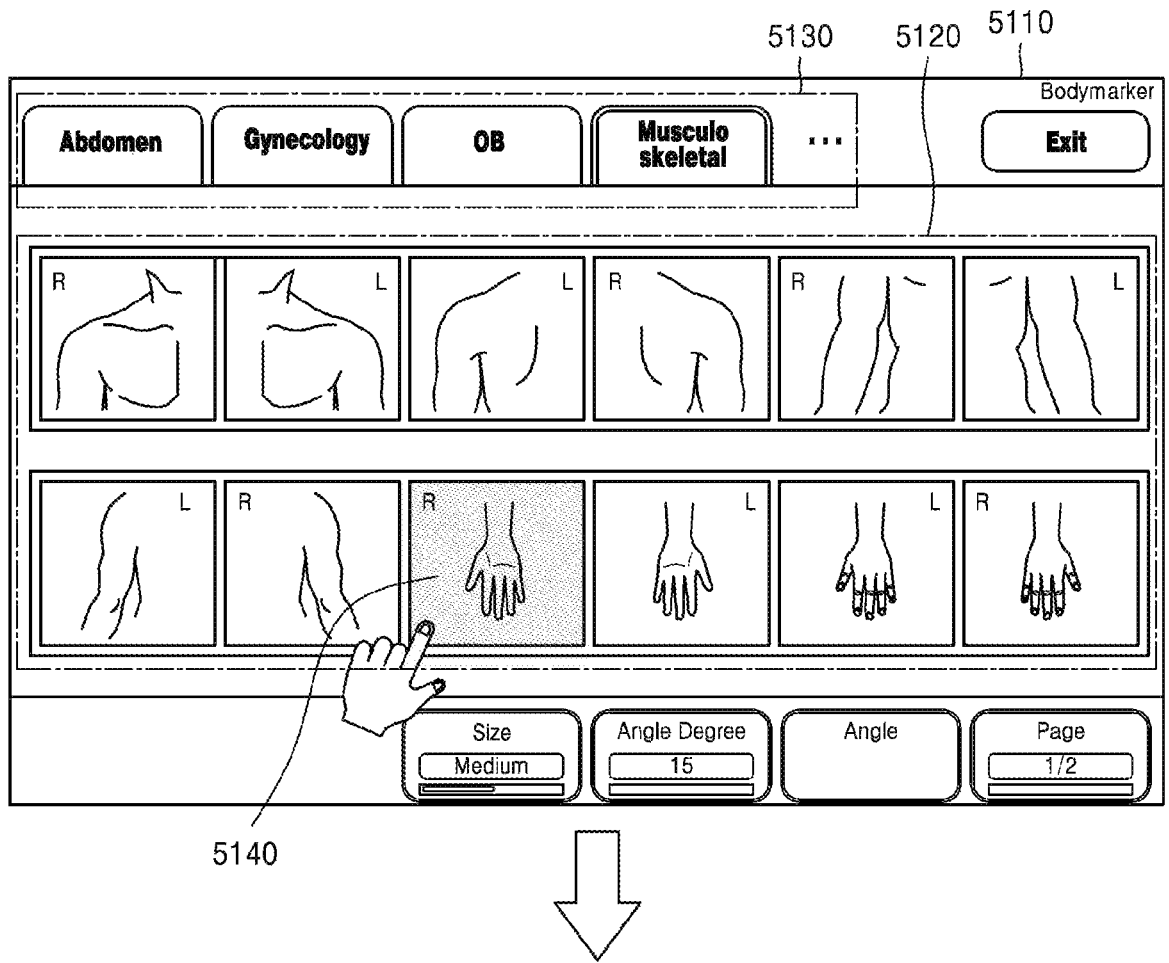
FIGS. 16A and 16B are diagrams illustrating an example of an input unit receiving a user input for selecting a first body marker, according to an exemplary embodiment.
Figure 16B:
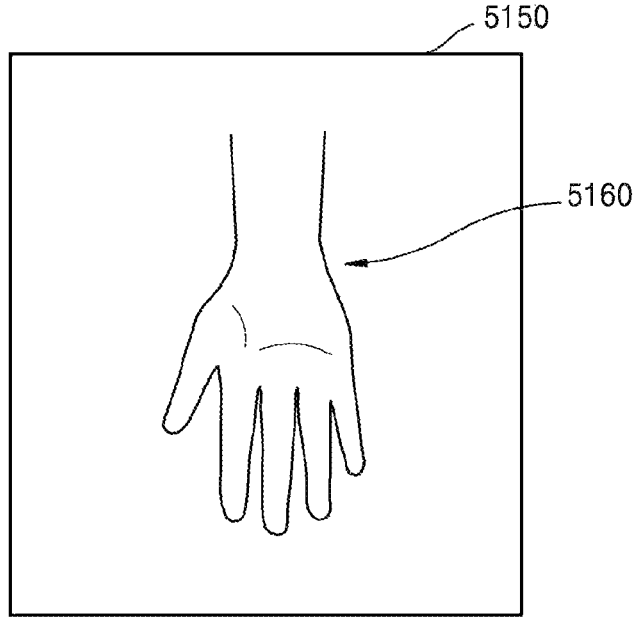

FIGS. 16A and 16B are diagrams illustrating an example of an input unit receiving a user input for selecting a first body marker, according to an exemplary embodiment.

Referring to FIG. 16A, a screen 5110 displays a plurality of body markers 5120 prestored in the apparatus 102. In this case, the body markers 5120 may be sorted into application groups 5130, as described above with reference to FIG. 5A.

The user may select a body marker 5140 from among the body markers 5120 displayed on the screen 5110. For example, when the input unit 1601 includes hardware components, such as a keyboard, a mouse, a trackball, and a jog switch, and a software module for driving the hardware components, the user may click the body marker 5140 from among the body markers 5120. As another example, when the input unit 1601 includes a touch screen and a software module for driving the touch screen, the user may tap the body marker 5140 from among the body markers 5120.

The controller 1702 may select a first body marker based on the user input. In other words, the body marker 5140 selected by the user is selected as the first body marker. Then, as shown in FIG. 16B, the display 1402 may display a first body marker 5160 on a screen 5150.

As described above with reference to FIG. 16A and FIG. 16B, the controller 1702 may select a body marker determined by the user as the first body marker. However, the exemplary embodiments are not limited thereto. For example, the controller 1702 may select the first body marker based on a shape of an object shown in a medical image. Hereinafter, an example of the controller 1702 selecting a first body marker based on a shape of an object will be described with reference to FIGS. 17, 18A, and 18B.

Figure 17:
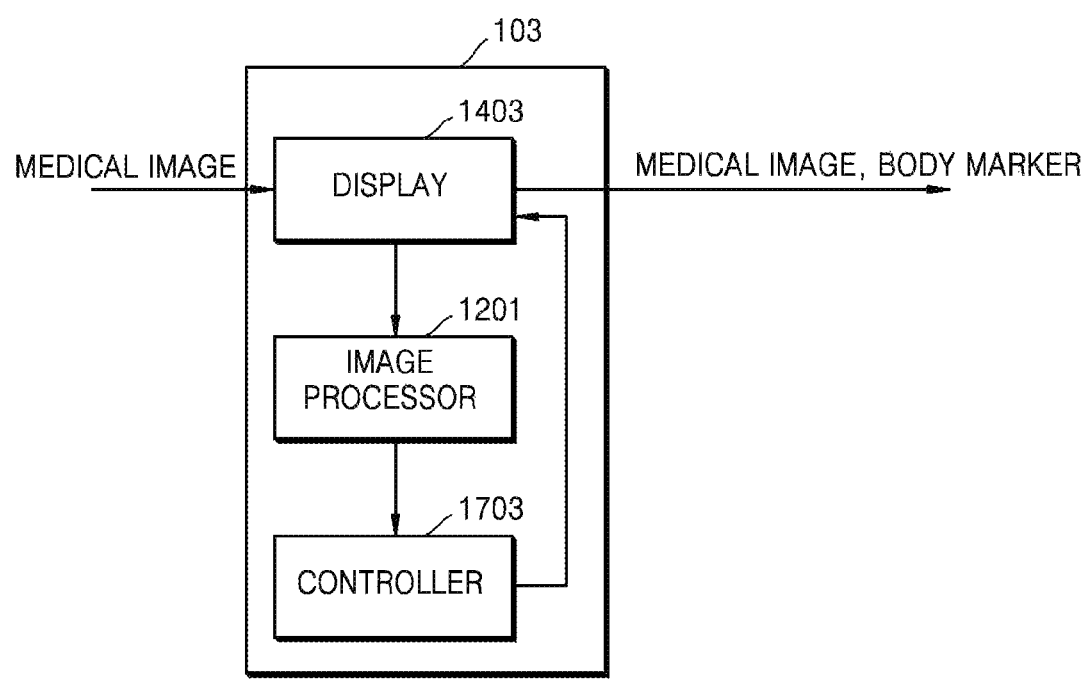
FIG. 17 is a block diagram illustrating an apparatus for generating a body marker, according to another exemplary embodiment.

FIG. 17 is a block diagram illustrating an apparatus 103 for generating a body marker, according to another exemplary embodiment.

Referring to FIG. 17, the apparatus 103 may include a controller 1703, a display 1403, and an image processor 1201. All or some of the controller 1703, the display 1403, and the image processor 1201 may be implemented as software modules, but are not limited thereto. Some of the controller 1703, the display 1403, and the image processor 1201 may be implemented as hardware. Also, each of the display 1403 and the image processor 1201 may include an independent control module.

Also, the controller 1703 may be the same as the controller 1701 of FIG. 4, the display 1403 may be the same as the display 1401 of FIG. 4, and the image processor 1201 may be the same as the image processor 1200 of FIG. 2. If the apparatus 103 is a component included in an ultrasound imaging device, then, in addition to the controller 1703, the display 1403, and the image processor 1201, the apparatus 103 may further include the ultrasound transceiver 1100, the communication module 1300, the memory 1500, and the input unit 1600 shown in FIG. 2.

Operations of the display 1403 are the same as operations of corresponding components described above with reference to FIGS. 4 to 14B. Therefore, detailed description of the display 1403 will not be repeated.

The image processor 1201 selects a portion of an object from a medical image. For example, the image processor 1201 may detect outlines of the object in the medical image, connect the detected outlines, and thus select the portion of the object. The image processor 1201 may select the portion of the object by using various methods, for example, a thresholding method, a K-means algorithm, a compression-based method, a histogram-based method, edge detection, a region-growing method, a partial differential equation-based method, and a graph partitioning method. Since the methods above are well-know to one of ordinary skill in the art, detailed descriptions thereof will be omitted.

The controller 1703 may select a first body marker based on information of the shape of the object. For example, from among a plurality of body markers stored in the apparatus 103, the controller 1703 may select a first body marker having a shape that is the most similar to the object.

Also, the controller 1703 may generate a second body marker by modifying the shape, orientations, or positions of the first body marker according to a user input received after the first body marker is selected. Since examples of the controller 1703 generating the second body marker have been described above in detail with reference to FIGS. 8A to 14B, the examples will not be repeatedly described.

Hereinafter an example of the image processor 1201 selecting the portion of the object from the medical image and the controller 1702 selecting the first body marker will be described in detail with reference to FIGS. 18A and 18B.

Figure 18A:
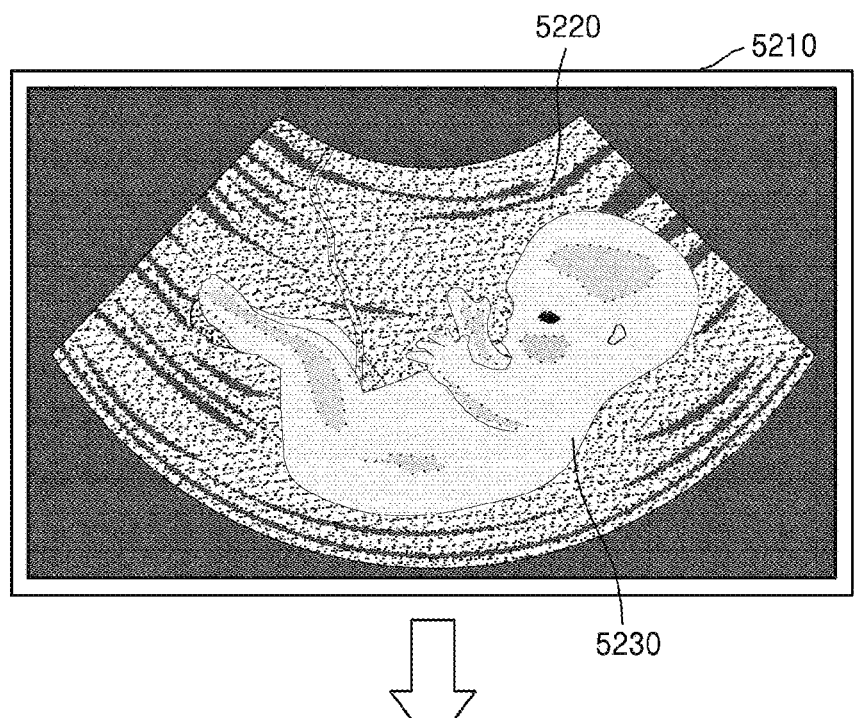
FIGS. 18A and 18B are diagrams illustrating an example of an image processor selecting a portion of an object from a medical image, according to an exemplary embodiment.
Figure 18B:
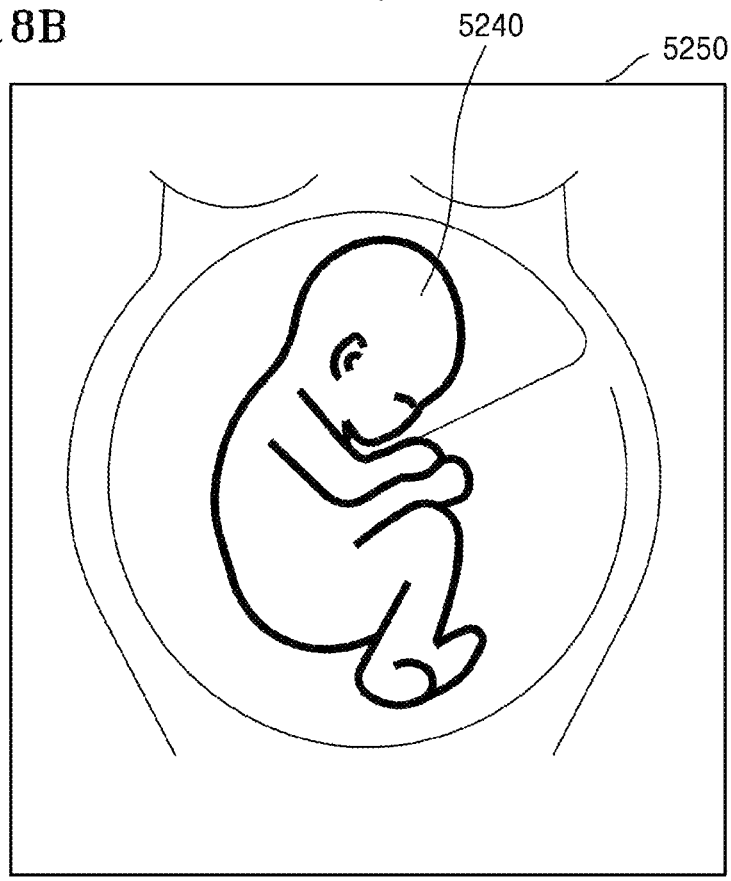

FIGS. 18A and 18B are diagrams illustrating an example of an image processor selecting a portion of an object from a medical image, according to an exemplary embodiment.

Referring to FIG. 18A, a screen 5210 displays a medical image 5220 showing an object 5230. The image processor 1201 may select a portion of the object 5230 from the medical image 5220. For example, the image processor 1201 may use any one of the methods described with reference to FIG. 17 to select the portion of the object 5230 from the medical image 5220.

The controller 1703 may select a first body marker based on the shape of the object 5230. For example, from among the plurality of body markers stored in the apparatus 103, the controller 1703 may select a body marker 5240 having a shape that is the most similar to the object 5230 as the first body marker. Also, as shown in FIG. 16B, the display 1402 may display the first body marker 5240 on a screen 5250.

Figure 19:
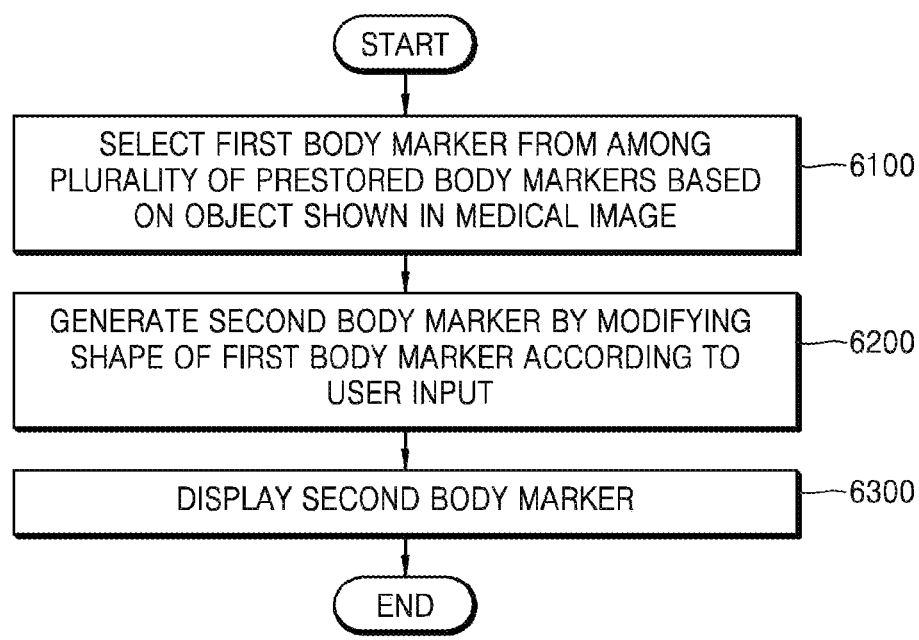
FIG. 19 is a flowchart illustrating a method of generating a body marker, according to an exemplary embodiment.

FIG. 19 is a flowchart illustrating a method of generating a body marker, according to an exemplary embodiment.

Referring to FIG. 19, the method of generating the body marker includes operations sequentially performed by the ultrasound diagnosis systems 1000, 1001, and 1002 respectively shown in FIGS. 1A, 1B and 2 or the apparatuses 100, 101, 102, and 103 respectively shown in FIGS. 4, 15, and 17. Therefore, all of the above-described features and elements of the ultrasound diagnosis systems 1000, 1001, and 1002 respectively shown in FIGS. 1A, 1B and 2 and the apparatuses 100, 101, 102, and 103 respectively shown in FIGS. 4, 15, and 17 apply to the method of FIG. 19.

In operation 6100, a controller selects a first body marker from among a plurality of prestored body markers based on an object shown in a medical image. The plurality of body markers may be stored in a memory of an apparatus for generating a body marker.

In operation 6200, the controller generates a second body marker by changing a shape of the first body marker according to a user input. For example, the controller may generate the second body marker by flipping the first body marker about a vertical axis according to the user input. As another example, the controller may generate the second body marker by rotating the first body marker about a central axis thereof according to the user input. Alternatively, the controller may generate the second body marker by rotating the first body marker in a clockwise or counterclockwise direction according to the user input.

In operation 6300, a display displays the second body marker. The display may display the first body marker and the second body marker on a single screen.

As described above, according to the one or more of the above exemplary embodiments, a body marker that corresponds to a current location or direction of an object shown in a medical image may be generated. Also, the user may spend less time selecting the body marker that corresponds to the current location or direction of the object from among prestored body markers.

In addition, other exemplary embodiments can also be implemented through computer-readable code/instructions in/on a medium, e.g., a computer-readable medium, to control at least one processing element to implement any above described exemplary embodiment. The medium can correspond to any medium/media permitting the storage and/or transmission of the computer-readable code.

The computer-readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer-readable code is stored/transferred and executed in a distributed fashion. Furthermore, the processing element could include a processor or a computer processor, and processing elements may be distributed and/or included in a single device.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of generating a body marker, the method comprising:
   selecting a first body marker having a first shape of an object from among a plurality of prestored body markers based on information of a current shape of the object, which is an organ of a human, shown in a medical image, wherein the first body marker shows a picture that represents the object in the medical image;
   displaying the first body marker and displaying guide images, that guide a change in the first shape, a position, or an orientation of the first body marker to modify the first body marker to be a second body marker, in the first body marker if the first body marker does not reflect the current shape or a location of the object shown in the medical image, wherein the guide images include a first guide image for rotating the first body marker along a predetermined central axis based on a first user input, a second guide image for rotating a portion of the first body marker toward the second guide image based on a second user input, and a third guide image for rotating the portion of the first body marker in clockwise or counterclockwise direction based on a third user input;
   receiving at least one user input of selecting a predetermined point on the guide images, dragging from one point to another point on the guide images, and flipping the first body marker about a predetermined axis of the first body marker to generate an inverse image of the first body marker as the second body marker;
   obtaining the second body marker that reflects the current shape or the location of the object by modifying the first body marker based on the at least one user input; and
   displaying the second body marker in the medical image of the object.

2. The method of claim 1, wherein the second body marker comprises a body marker generated by flipping the first body marker about a vertical axis.

3. The method of claim 1, wherein the second body marker comprises a body marker generated by flipping the first body marker about a horizontal axis.

4. The method of claim 1, wherein the second body marker comprises a body marker generated by rotating the first body marker about a central axis of the first body marker.

5. The method of claim 1, wherein the second body marker comprises a body marker generated by rotating the first body marker in a clockwise direction.

6. The method of claim 1, wherein the second body marker comprises a body marker generated by rotating the first body marker in a counterclockwise direction.

7. The method of claim 1, wherein the selecting comprises receiving a fourth user input for selecting the first body marker that corresponds to the object from among a plurality of prestored body markers, and selecting the first body marker based on the fourth user input.

8. The method of claim 1, wherein the selecting comprises selecting a portion of the object shown in the medical image, and selecting the first body marker based on the selected portion of the object.

9. The method of claim 1, wherein the plurality of prestored body markers are sorted into application groups.

10. The method of claim 1, wherein the first body marker and the second body marker are 2-dimensional or 3-dimensional.

11. The method of claim 1, wherein the at least one user input comprises a user gesture input on a touch screen.

12. The method of claim 1, wherein the at least one user input is input via a mouse or at least one key on a keyboard.

13. The method of claim 1, wherein the displaying comprises displaying the first and second body markers on a single screen.

14. A non-transitory computer-readable recording medium having recorded thereon a program, which, when executed by a computer, performs the method of claim 1.

15. An apparatus for generating a body marker, the apparatus comprising:
a display configured to display a medical image showing an object, which is an organ of a human; and
a controller configured to select a first body marker having a first shape of the object from among a plurality of prestored body markers based on information of a current shape of the object, and generate a second body marker, wherein the first body marker shows a picture that represents the object in the medical image,
wherein the display is further configured to display the first body marker and display guide images, that guide a change in the first shape, a position, or an orientation of the first body marker to modify the first body marker to be a second body marker, in the first body marker if the first body marker does not reflect the current shape or a location of the object shown in the medical image, wherein the guide images include a first guide image for rotating the first body marker along a predetermined central axis based on a first user input, a second guide image for rotating a portion of the first body marker toward the second guide image based on a second user input, and a third guide image for rotating the portion of the first body marker in clockwise or counterclockwise direction based on a third user input,
wherein the apparatus further comprises an input device configured to receive at least one user input of selecting a predetermined point on the guide images, dragging from one point to another point on the guide images, and flipping the first body marker about a predetermined axis of the first body marker to generate an inverse image of the first body marker as the second body marker,
wherein the controller is further configured to generate the second body marker that reflects the current shape or the location of the object by modifying the first body marker based on the at least one user input,
wherein the display displays the second body marker in the medical image of the object.

16. The apparatus of claim 15, wherein the second body marker comprises a body marker generated by flipping the first body marker about a vertical axis.

17. The apparatus of claim 15, wherein the second body marker comprises a body marker generated by flipping the first body marker about a horizontal axis.

18. The apparatus of claim 15, wherein the second body marker comprises a body marker generated by rotating the first body marker about a central axis of the first body marker.

19. The apparatus of claim 15, wherein the second body marker comprises a body marker generated by rotating the first body marker in a clockwise direction.

20. The apparatus of claim 15, wherein the second body marker comprises a body marker generated by rotating the first body marker in a counterclockwise direction.

21. The apparatus of claim 15, wherein the input device is further configured to receive a fourth user input for selecting the first body marker that corresponds to the object from among a plurality of prestored body markers, and
wherein the controller selects the first body marker based on the fourth user input.

22. The apparatus of claim 15, further comprising an image processor configured to select a portion of the object from the medical image, and
wherein the controller selects the first body marker based on the selected portion of the object.

23. The apparatus of claim 15, wherein the plurality of prestored body markers are sorted into application groups.

24. The apparatus of claim 15, wherein the first body marker and the second body marker are 2-dimensional or 3-dimensional.

25. The apparatus of claim 15, wherein the at least one user input comprises a user gesture input on a touch screen.

26. The apparatus of claim 15, wherein the at least one user input is input via a mouse or at least one key on a keyboard.

27. The apparatus of claim 15, wherein the display displays the first and second body markers on a single screen.

28. An ultrasound diagnosis system comprising:
a probe configured to transmit ultrasound signals to an object and receive echo signals that correspond to the ultrasound signals;
a display;
an ultrasound imaging device;
a memory storing instructions that, when executed by the ultrasound imaging device, perform operations comprising:
generating a medical image showing the object, which is an organ of a human, based on the echo signals;
displaying the medical image;
selecting a first body marker having a first shape of the object from among a plurality of prestored body markers based on information of a current shape of the object shown in the medical image, wherein the first body marker shows a picture that represents the object in the medical image;
displaying the first body marker and displaying guide images, that guide a change in the first shape, a position, or an orientation of the first body marker to modify the first body marker to be a second body marker, in the first body marker if the first body marker does not reflect a current shape or a location of the object shown in the medical image, wherein the guide images include a first guide image for rotating the first body marker along a predetermined central axis based on a first user input, a second guide image for rotating a portion of the first body marker toward the second guide image based on a second user input, and a third guide image for rotating the portion of the first body marker in clockwise or counterclockwise direction based on a third user input;
receiving at least one user input of selecting a predetermined point on the guide images, dragging from one point to another point on the guide images, and flipping the first body marker about a predetermined axis of the first body marker to generate an inverse image of the first body marker as the second body marker;
obtaining the second body marker that reflects the current shape or the location of the object by modifying a shape of the first body marker based on the at least one user input; and
displaying the second body marker in the medical image of the object.

29. The method of claim 1, wherein the first body marker and the second body marker comprise an outline image of the organ of the human, and wherein the second body marker comprising the outline image of the organ is displayed together with the medical image including a real image of the organ.

30. The method of claim 1, wherein the guide images provide guidance on a three dimensional movement of the first body marker.

\* \* \* \* \*